United States Patent
Sokolov et al.

(10) Patent No.: US 12,233,230 B2
(45) Date of Patent: Feb. 25, 2025

(54) SINGLE-USE DISPOSABLE SET CONNECTOR

(71) Applicant: BAYER HEALTHCARE LLC, Whippany, NJ (US)

(72) Inventors: Richard Sokolov, Earlwood (AU); Alison Ruth Von Moger, Carnegie (AU); Benjamin James Cullen, Beecroft (AU); Ernesto Hueso Monis, Glen Huntly (AU); Kamman Law, Burwood (AU); Mark Silvio Profaca, West Pymble (AU); John A. Haury, Sewickley, PA (US); Michael Swantner, Saxonburg, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1027 days.

(21) Appl. No.: 16/773,150

(22) Filed: Jan. 27, 2020

(65) Prior Publication Data

US 2020/0155823 A1    May 21, 2020

Related U.S. Application Data

(63) Continuation of application No. 15/110,243, filed as application No. PCT/US2015/010825 on Jan. 9, 2015, now Pat. No. 10,549,084.

(Continued)

(51) Int. Cl.
*A61M 39/10*    (2006.01)
*A61M 5/00*    (2006.01)

(52) U.S. Cl.
CPC ........ *A61M 39/1011* (2013.01); *A61M 5/007* (2013.01); *A61M 2039/1027* (2013.01);
(Continued)

(58) Field of Classification Search
CPC ...... A61M 39/1011; A61M 2039/1044; A61M 39/1033; A61M 39/12; A61M 2039/1027;
(Continued)

(56) References Cited

U.S. PATENT DOCUMENTS

| 926,755 A | 7/1909 | Nathaniel |
| 2,287,746 A | 6/1942 | Morton |

(Continued)

FOREIGN PATENT DOCUMENTS

| CA | 1126117 A | 6/1982 |
| CA | 2227973 A1 | 3/1997 |

(Continued)

OTHER PUBLICATIONS

Asepti-Quik S Connector Catalog, May 2010.
(Continued)

*Primary Examiner* — Kami A Bosworth
(74) *Attorney, Agent, or Firm* — Joseph L. Kent; James R. Stevenson

(57) ABSTRACT

A medical connector for providing a sterile connection between a multi-use portion and a single-use portion of a fluid delivery system is provided. The medical connector includes a fluid inlet port configured for removable engagement with a connection port of a multi-use disposable set (MUDS) to establish a fluid connection therewith and a waste outlet port configured for removable engagement with a waste inlet port of the MUDS to establish a fluid connection therewith. A patient fluid line is connected, at a first end, to the fluid inlet port and connected, at a second end, to the waste outlet port. Fluid flow through the patient fluid line is unidirectional from the first end to the second end. The patient fluid line is configured for being disconnected from (Continued)

the waste outlet port for delivering fluid to a patient. A multi-fluid delivery system having the medical connector and MUDS is also provided.

18 Claims, 22 Drawing Sheets

Related U.S. Application Data

(60) Provisional application No. 61/925,940, filed on Jan. 10, 2014.

(52) U.S. Cl.
CPC ............ *A61M 2039/1033* (2013.01); *A61M 2039/1094* (2013.01); *A61M 2205/12* (2013.01); *A61M 2205/3584* (2013.01); *A61M 2205/50* (2013.01); *A61M 2205/502* (2013.01); *A61M 2205/52* (2013.01)

(58) Field of Classification Search
CPC .......... A61M 2039/1094; A61M 5/162; A61M 39/00; A61M 39/08; A61M 39/10; A61M 2039/0009; A61M 2039/1005; A61M 2039/1016; A61M 2039/1022; A61M 2205/14; A61M 2205/6018; A61M 2205/6027; A61M 2205/6036; A61M 2205/6045; A61M 2205/6063
See application file for complete search history.

(56) References Cited

U.S. PATENT DOCUMENTS

| | | |
|---|---|---|
| 2,731,053 A | 1/1956 | Lockhart |
| 2,780,243 A | 2/1957 | Williams et al. |
| 2,798,487 A | 7/1957 | Ferguson |
| 2,938,238 A | 5/1960 | Gewecke et al. |
| 2,997,043 A | 8/1961 | Flynn |
| 3,164,279 A | 1/1965 | Towns |
| 3,658,061 A | 4/1972 | Hall |
| 3,835,862 A | 9/1974 | Villari |
| 3,909,910 A | 10/1975 | Rowe et al. |
| 3,985,133 A | 10/1976 | Jenkins et al. |
| 3,986,508 A | 10/1976 | Barrington |
| 3,987,930 A | 10/1976 | Fuson |
| 4,019,512 A | 4/1977 | Tenczar |
| 4,022,205 A | 5/1977 | Tenczar |
| 4,106,654 A | 8/1978 | Jones |
| 4,123,091 A | 10/1978 | Cosentino et al. |
| 4,187,846 A | 2/1980 | Carminucci et al. |
| 4,194,509 A | 3/1980 | Ferguson et al. |
| 4,227,615 A | 10/1980 | Flick |
| 4,230,231 A | 10/1980 | Burnett et al. |
| 4,340,148 A | 7/1982 | Beckham |
| 4,360,969 A | 11/1982 | Collier |
| 4,366,816 A | 1/1983 | Bayard et al. |
| 4,369,779 A | 1/1983 | Spencer |
| 4,396,385 A | 8/1983 | Kelly et al. |
| 4,398,757 A | 8/1983 | Floyd et al. |
| 4,402,420 A | 9/1983 | Chernack |
| 4,433,973 A | 2/1984 | Kurtz et al. |
| 4,450,624 A | 5/1984 | Collier |
| 4,482,347 A | 11/1984 | Borsanyi |
| 4,511,359 A | 4/1985 | Vaillancourt |
| 4,551,146 A | 11/1985 | Rogers |
| 4,559,043 A | 12/1985 | Whitehouse et al. |
| 4,579,823 A | 4/1986 | Ryder |
| 4,624,664 A | 11/1986 | Peluso et al. |
| 4,636,204 A | 1/1987 | Christopherson et al. |
| 4,687,472 A | 8/1987 | Gross |
| 4,723,945 A | 2/1988 | Theiling |
| 4,775,369 A | 10/1988 | Schwartz |
| 4,778,447 A | 10/1988 | Velde et al. |
| 4,795,426 A | 1/1989 | Jones |
| 4,810,241 A | 3/1989 | Rogers |
| 4,828,557 A | 5/1989 | Persidsky |
| 4,854,836 A | 8/1989 | Borsanyi |
| 4,883,641 A | 11/1989 | Wicks et al. |
| 4,950,260 A | 8/1990 | Bonaldo |
| 4,981,469 A | 1/1991 | Whitehouse et al. |
| 5,049,047 A | 9/1991 | Polaschegg et al. |
| 5,057,088 A | 10/1991 | Narayanan et al. |
| 5,088,984 A | 2/1992 | Fields |
| 5,098,395 A | 3/1992 | Fields |
| 5,102,253 A | 4/1992 | Pugliesi-Conti et al. |
| 5,171,229 A | 12/1992 | Mcneil et al. |
| 5,184,742 A | 2/1993 | Decaprio et al. |
| 5,213,483 A | 5/1993 | Flaherty et al. |
| 5,221,267 A | 6/1993 | Folden |
| 5,247,434 A * | 9/1993 | Peterson ............... G06F 3/0482 |
| | | 700/83 |
| 5,251,873 A | 10/1993 | Atkinson et al. |
| 5,280,809 A | 1/1994 | Tive |
| 5,281,111 A | 1/1994 | Plambeck et al. |
| 5,292,308 A | 3/1994 | Ryan |
| 5,340,359 A | 8/1994 | Segura Badia |
| 5,382,242 A | 1/1995 | Horton et al. |
| 5,413,280 A | 5/1995 | Taylor |
| 5,482,171 A | 1/1996 | Palmer |
| 5,494,036 A | 2/1996 | Uber, III et al. |
| 5,498,253 A | 3/1996 | Aswad et al. |
| 5,522,803 A * | 6/1996 | Teissen-Simony ... A61M 5/158 |
| | | 604/93.01 |
| 5,551,850 A | 9/1996 | Williamson et al. |
| 5,569,181 A | 10/1996 | Heilman et al. |
| 5,620,433 A | 4/1997 | Aswad et al. |
| 5,702,371 A * | 12/1997 | Bierman ............... A61M 25/02 |
| | | 604/174 |
| 5,739,508 A | 4/1998 | Uber |
| 5,746,718 A | 5/1998 | Steyn |
| 5,779,675 A | 7/1998 | Reilly et al. |
| 5,785,691 A | 7/1998 | Vetter et al. |
| 5,803,510 A | 9/1998 | Dorsey, III et al. |
| 5,806,519 A | 9/1998 | Evans, III et al. |
| 5,840,026 A | 11/1998 | Uber, III et al. |
| 5,843,037 A | 12/1998 | Uber, III |
| 5,853,096 A | 12/1998 | Bartur et al. |
| 5,873,861 A | 2/1999 | Hitchins et al. |
| 5,913,434 A | 6/1999 | Fukuhara et al. |
| 5,916,197 A | 6/1999 | Reilly et al. |
| 5,934,496 A | 8/1999 | Mogard et al. |
| 5,964,583 A | 10/1999 | Danby |
| 5,972,292 A | 10/1999 | Demeo |
| 6,077,259 A | 6/2000 | Caizza et al. |
| 6,113,068 A | 9/2000 | Ryan |
| 6,123,686 A | 9/2000 | Olsen et al. |
| 6,164,279 A | 12/2000 | Tweedle |
| 6,261,270 B1 | 7/2001 | Gault et al. |
| 6,306,117 B1 | 10/2001 | Uber, III |
| 6,339,718 B1 | 1/2002 | Zatezalo et al. |
| 6,428,518 B1 | 8/2002 | Brengle et al. |
| 6,436,072 B1 | 8/2002 | Kullas et al. |
| 6,511,472 B1 | 1/2003 | Hayman et al. |
| 6,666,839 B2 | 12/2003 | Utterberg et al. |
| 6,669,681 B2 | 12/2003 | Jepson et al. |
| 6,679,529 B2 | 1/2004 | Johnson et al. |
| 6,814,726 B1 | 11/2004 | Lauer |
| 6,821,267 B2 | 11/2004 | Veillon et al. |
| 6,851,427 B1 * | 2/2005 | Nashed ............... A61M 16/0816 |
| | | 128/207.14 |
| 6,869,425 B2 | 3/2005 | Briggs et al. |
| 6,911,025 B2 | 6/2005 | Miyahara |
| 6,981,960 B2 | 1/2006 | Cho et al. |
| 7,022,256 B2 | 4/2006 | Jegami et al. |
| 7,040,598 B2 | 5/2006 | Raybuck |
| 7,070,589 B2 | 7/2006 | Ebner et al. |
| 7,083,605 B2 | 8/2006 | Miyahara |
| 7,097,209 B2 | 8/2006 | Unger et al. |
| 7,241,285 B1 | 7/2007 | Dikeman |
| 7,252,308 B2 | 8/2007 | Thilly |
| 7,374,555 B2 | 5/2008 | Heinz et al. |
| 7,452,349 B2 | 11/2008 | Miyahara et al. |

(56) References Cited

U.S. PATENT DOCUMENTS

| | | |
|---|---|---|
| 7,481,795 B2 | 1/2009 | Thompson et al. |
| 7,569,047 B2 | 8/2009 | Utterberg |
| 7,618,412 B2 | 11/2009 | Chernack |
| 7,713,250 B2 | 5/2010 | Harding et al. |
| 7,731,155 B2 | 6/2010 | Funamura et al. |
| 7,740,288 B2 | 6/2010 | Mantell |
| 7,918,243 B2 | 4/2011 | Diodati et al. |
| 7,938,454 B2 | 5/2011 | Buchanan et al. |
| 8,007,487 B2 | 8/2011 | Patrick et al. |
| 8,012,144 B2 | 9/2011 | Moberg |
| 8,038,667 B2 | 10/2011 | Racz et al. |
| 8,062,009 B2 | 11/2011 | Cueni |
| 8,133,035 B2 | 3/2012 | Wolff |
| 8,140,274 B2 | 3/2012 | Gagel et al. |
| 8,147,464 B2 | 4/2012 | Spohn et al. |
| 8,157,547 B2 | 4/2012 | Oude et al. |
| 8,257,267 B2 | 9/2012 | Thornton |
| 8,287,724 B2 | 10/2012 | Slepicka et al. |
| 8,308,456 B2 | 11/2012 | Moubayed |
| 8,343,128 B2 | 1/2013 | Nagao et al. |
| 8,360,757 B2 | 1/2013 | Knauper et al. |
| 8,425,463 B2 | 4/2013 | Patrick et al. |
| 8,545,440 B2 | 10/2013 | Patrick et al. |
| 8,852,162 B2 | 10/2014 | Williams et al. |
| 9,044,542 B2 | 6/2015 | Patrick et al. |
| 9,358,333 B2 | 6/2016 | Trombley, III et al. |
| 9,393,441 B2 | 7/2016 | Hoffman et al. |
| 9,408,971 B2 | 8/2016 | Carlyon et al. |
| 9,566,381 B2 | 2/2017 | Barron et al. |
| 10,046,106 B2 | 8/2018 | Cowan et al. |
| 10,420,902 B2 | 9/2019 | Cowan et al. |
| 10,507,319 B2 | 12/2019 | Haury et al. |
| 2001/0016704 A1 | 8/2001 | Zadno-Azizi et al. |
| 2002/0010437 A1 | 1/2002 | Lopez et al. |
| 2002/0093192 A1 | 7/2002 | Matkovich |
| 2004/0111078 A1 | 6/2004 | Miyahara |
| 2004/0122369 A1 | 6/2004 | Schriver et al. |
| 2004/0227120 A1 | 11/2004 | Raybuck |
| 2005/0090805 A1 | 4/2005 | Shaw et al. |
| 2005/0199304 A1 | 9/2005 | Poppe et al. |
| 2005/0267418 A1 | 12/2005 | Fournie et al. |
| 2006/0042638 A1* | 3/2006 | Niklewski ......... A61M 16/0858 128/207.18 |
| 2007/0049870 A1 | 3/2007 | Gray et al. |
| 2007/0088271 A1 | 4/2007 | Richards |
| 2007/0100282 A1 | 5/2007 | Small et al. |
| 2008/0045925 A1 | 2/2008 | Stepovich et al. |
| 2008/0071219 A1 | 3/2008 | Rhinehart et al. |
| 2008/0071220 A1 | 3/2008 | Rhinehart et al. |
| 2008/0086087 A1* | 4/2008 | Spohn ................. A61M 5/1408 604/151 |
| 2008/0097342 A1 | 4/2008 | Gordin |
| 2008/0177250 A1 | 7/2008 | Howlett et al. |
| 2008/0287872 A1 | 11/2008 | Patzer |
| 2009/0102192 A1 | 4/2009 | Ziman |
| 2009/0105629 A1 | 4/2009 | Grant et al. |
| 2009/0163858 A1* | 6/2009 | Haddad ................ A61M 5/365 604/67 |
| 2009/0182309 A1 | 7/2009 | Muffly |
| 2009/0216192 A1 | 8/2009 | Schriver et al. |
| 2010/0010443 A1* | 1/2010 | Morgan ............ A61M 5/14244 604/151 |
| 2010/0022988 A1 | 1/2010 | Wochner et al. |
| 2010/0049170 A1 | 2/2010 | Solomon et al. |
| 2010/0056975 A1* | 3/2010 | Dale ...................... A61M 1/16 604/6.16 |
| 2010/0113924 A1 | 5/2010 | Hajicek et al. |
| 2010/0116365 A1 | 5/2010 | Mccarty |
| 2010/0130918 A1 | 5/2010 | Elahi |
| 2010/0130922 A1 | 5/2010 | Borlaug et al. |
| 2010/0286467 A1 | 11/2010 | Pesach et al. |
| 2010/0305508 A1 | 12/2010 | Franks et al. |
| 2011/0049866 A1 | 3/2011 | Trombley, III et al. |
| 2011/0054440 A1 | 3/2011 | Lewis |
| 2011/0196291 A1 | 8/2011 | Vischer et al. |
| 2011/0208047 A1* | 8/2011 | Fago ................. A61M 5/1407 600/432 |
| 2011/0240158 A1 | 10/2011 | Py |
| 2011/0282302 A1 | 11/2011 | Lopez et al. |
| 2011/0313394 A1 | 12/2011 | Bobo, Sr. |
| 2012/0116317 A1 | 5/2012 | Kassab et al. |
| 2012/0123257 A1 | 5/2012 | Stokes, Jr. et al. |
| 2012/0123392 A1* | 5/2012 | McKinnon ............ A61M 39/10 604/533 |
| 2012/0148415 A1 | 6/2012 | Brueckner et al. |
| 2012/0284991 A1* | 11/2012 | Kusz ................... A61M 39/12 137/315.01 |
| 2013/0079581 A1 | 3/2013 | Agamaite et al. |
| 2013/0123567 A1 | 5/2013 | Agamaite et al. |
| 2013/0131579 A1 | 5/2013 | Mantell et al. |
| 2013/0211248 A1 | 8/2013 | Cowan et al. |
| 2013/0245565 A1 | 9/2013 | Leak et al. |
| 2013/0263850 A1* | 10/2013 | Acker ................. A61M 16/202 128/203.14 |
| 2013/0331634 A1 | 12/2013 | Kaintz et al. |
| 2014/0107480 A1 | 4/2014 | Spohn et al. |
| 2014/0107579 A1* | 4/2014 | Lanigan ................ A61M 39/10 604/151 |
| 2014/0224829 A1 | 8/2014 | Capone et al. |
| 2014/0296786 A1 | 10/2014 | Servansky et al. |
| 2014/0342447 A1 | 11/2014 | Aviles et al. |
| 2015/0133859 A1* | 5/2015 | Caspers .............. A61M 5/5086 604/110 |
| 2015/0174338 A1 | 6/2015 | Takemoto |
| 2015/0192234 A1* | 7/2015 | Fries ..................... A61M 39/10 285/9.1 |
| 2016/0015885 A1* | 1/2016 | Pananen ............... A61M 39/12 604/111 |

FOREIGN PATENT DOCUMENTS

| | | |
|---|---|---|
| CA | 2574551 A1 | 7/2008 |
| DE | 3838689 C1 | 6/1990 |
| DE | 4037797 C1 | 2/1992 |
| DE | 102013104018 A1 | 10/2014 |
| EP | 0204977 A1 | 12/1986 |
| EP | 0503670 A2 | 9/1992 |
| EP | 1331020 A1 | 7/2003 |
| EP | 2409720 A1 | 1/2012 |
| EP | 1834664 B1 | 5/2013 |
| FR | 2594496 A1 | 8/1987 |
| FR | 2847342 A1 | 5/2004 |
| GB | 2020735 A | 11/1979 |
| JP | 2003210574 A | 7/2003 |
| JP | 6184495 B2 | 8/2017 |
| WO | 9103404 A1 | 3/1991 |
| WO | 9714493 A1 | 4/1997 |
| WO | 9806446 A2 | 2/1998 |
| WO | 0202164 A1 | 1/2002 |
| WO | 0204049 A1 | 1/2002 |
| WO | 02096487 A1 | 12/2002 |
| WO | 03039646 A1 | 5/2003 |
| WO | 03044488 A1 | 5/2003 |
| WO | 2005062015 A1 | 7/2005 |
| WO | 2005110007 A2 | 11/2005 |
| WO | 2008086631 A1 | 7/2008 |
| WO | 2008141337 A1 | 11/2008 |
| WO | 2009067200 A2 | 5/2009 |
| WO | 2009149367 A1 | 12/2009 |
| WO | 2011064240 A1 | 6/2011 |
| WO | 2012170961 A1 | 12/2012 |
| WO | 2013043868 A1 | 3/2013 |
| WO | 2013043881 A1 | 3/2013 |
| WO | 2013059563 A1 | 4/2013 |
| WO | 2013104665 A1 | 7/2013 |
| WO | 2015066506 A2 | 5/2015 |

OTHER PUBLICATIONS

AseptiQuik X Connector Catalog, Oct. 2012.

Catalog Valves, http://www.minivalve.com/newsite/index.php/en/

(56) References Cited

OTHER PUBLICATIONS home—last visited Sep. 23, 2016.
Colder; Products Company., "Asepti-Quik Product Catalog", accessed online on Oct. 11, 2013.
Connection Solutions for Biopharmaceutical Processes, May 2012.
DoseGuard Valved Bottle Adapter System Brochure.
"Extended European Search Report and Written Opinion from EP14810311", Nov. 22, 2016.
"Extended European Search Report from EP App. No. 16735394", Dec. 11, 2018.
Hadaway; Lynn., "Needleless Connectors: a Primer on Terminology", Journal of Infusion Nursing, Jan./Feb. 2010, 33(1), 22-31.
"International Preliminary Report on Patentability and Written Opinion from PCT Application No. PCT/US2012/060978", Apr. 22, 2014.
International Preliminary Report on Patentability and Written Opinion from PCT Application No. PCT/US2014/042310 mailed Dec. 19, 2014.
"International Preliminary Report on Patentability from PCT Application No. PCT/US2015/010825", Jul. 21, 2016.
International Preliminary Report on Patentability, Written Opinion, and International Search Report from PCT/US2014/042310 dated Dec. 15, 2015.
"International Search Report and Written Opinion from corresponding PCT App. No. PCT/US2014/042310", Dec. 19, 2014.
"International Search Report and Written Opinion from corresponding PCT App. No. PCT/US2015/010825", Apr. 10, 2015.
"International Search Report and Written Opinion from PCT Application No. PCT/US2014/044500", Nov. 4, 2014.
"International Search Report from PCT Application No. PCT/US2012/060978", Feb. 5, 2013.
"International Search Report in PCT Application No. PCT/US2014/044500", Nov. 4, 2014.
Pure Fit SC True Sterile Connections . . . Outside the Clean Room Catalog, Saint-Gobain Performance Plastics. 2008.
ReadyMate Disposable Aseptic Connectors, Operation Manual, Jul. 2009.
Single-Use Bags 50 to 500 Liters Catalog, Jun. 2010.
Site-Scrub IPA Device—last visited Sep. 23, 2016.
Takeone Aseptic Sampling System Brochure, 2010.
UFP; Technologies., "BioShell Suspension Pack Brochure", accessed online on May 7, 2013.
"Ultraport Swabbable Port Stopcocks, B. Braun Sharing Expertise.", accessed online on Apr. 14, 2014.
"Supplementary European Search Report from EP Application No. 15735396", Jun. 28, 2017.
"Supplementary European Search Report from EP Application No. EP12842335.", Feb. 16, 2015.
"Written Opinion and International Search Report from PCT Application No. PCT/US2016/012434", May 6, 2016.

\* cited by examiner

SINGLE-USE DISPOSABLE SET CONNECTOR

CROSS-REFERENCE TO RELATED APPLICATIONS

This application is a continuation under 37 C.F.R § 1.53(b) and claims priority under 35 U.S.C. § 120 to U.S. application Ser. No. 15/110,243, filed Jul. 7, 2016, which is a 371 national phase application of PCT International Application No. PCT/US2015/010825, filed Jan. 9, 2015, and designating the United States of America, which claims priority to U.S. Provisional Patent Application No. 61/925,940, filed Jan. 10, 2014, the disclosures of which are incorporated herein by reference in their entirety.

BACKGROUND

Field

This disclosure relates, in general, to the field of single-use disposable set connectors, and, more particularly, to single-use disposable set connectors configured for delivering fluid to a patient.

Description of the Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these medical fluid delivery systems are designed to deliver a preset amount of fluid at a preset flow rate.

In some injection procedures, the medical practitioner places a catheter or needle into a vein or artery of the patient. The catheter or needle is connected to either a manual or an automatic fluid injector system by way of tubing and a connector that interfaces with the fluid injector system. Automatic fluid injector systems typically include at least one syringe connected to at least one fluid injector having, for example, a powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each. A single-use disposable set connector and associated tubing is connected to the fluid injector system for delivering one or more fluids to the patient.

While various manual and automatic fluid delivery systems are known in the medical field, improved multi-fluid delivery systems adapted for use in medical diagnostic and therapeutic procedures where one or more fluids are supplied to a patient during such procedures continue to be in demand. Additionally, improved single-use disposable set connectors that may be used with multi-fluid delivery systems for facilitating a delivery of one or more fluids to a patient are also desired in the medical field. The medical field continues to demand improved medical devices and systems used to supply fluids to patients during various medical procedures.

SUMMARY

In view of the foregoing, a need exists for a medical connector assembly for connecting a single-use portion of a medical assembly to a multi-use portion of the assembly. Further, there is a need for a fluid delivery system for delivery of multiple fluid doses to multiple patients using one or more multi-dose containers. The assembly should be configured to retain sterility of the fluid path through the single-use and multi-use portions of the assembly and, particularly, should maintain sterility of portions of the assembly which are reusable. Furthermore, the system should be arranged to permit automatic priming, defined as removing air from the fluid line, for easier fluid injections.

Therefore, a medical connector configured to address some or all of these needs is provided herein. In accordance with one embodiment, a medical connector may include a fluid inlet port configured for removable engagement with a connection port of a multi-use disposable set (MUDS) to establish a fluid connection therewith. The medical connector may further include a waste outlet port configured for removable engagement with a waste inlet port of the MUDS to establish a fluid connection therewith. A patient fluid line may be connected, at a first end, to the fluid inlet port and may be connected, at a second end, to the waste outlet port. Fluid flow through the patient fluid line may be unidirectional from the first end to the second end. The patient fluid line may be configured for being reversibly disconnected from the waste outlet port for delivering fluid to a patient.

In accordance with another embodiment, the medical connector may have a locking mechanism for removably securing the medical connector to the MUDS. The locking mechanism may have a flexible tab that is deflectable between an engaged position and a disengaged position by deflecting at least a portion of the flexible tab. The flexible tab may have a pressing surface that, when pressed, deflects the flexible tab from the engaged position to the disengaged position. In some embodiments, the fluid inlet port may have a shroud surrounding at least a portion of the fluid inlet port. The shroud may have at least one indentation to facilitate handling of the medical connector. The shroud may have one or more ribs protruding from an outer surface of the shroud. The fluid inlet port may be shaped to prevent connection with the waste inlet port of the MUDS and wherein the waste outlet port is shaped to prevent connection with the connection port of the MUDS. The medical connector may have an asymmetrical shape such that the medical connector is connectable with the MUDS in one orientation only. At least one fin may be provided to prevent erroneous connection of the medical connector with the MUDS. In some embodiments, the second end of the patient fluid line may have a connector configured for removable engagement with the waste outlet port while maintaining sterility of the second end. The connector may be in fluid communication with the waste outlet port. The connector may be a luer-lock connector. A one-way valve may be configured for maintaining unidirectional flow through the fluid inlet port into the patient fluid line. In some embodiments, at least one sensor element may be configured for interacting with at least one sensor configured for detecting a presence or absence of the at least one sensor element indicating that the medical connector has been properly inserted or installed. The at least one sensor element has one or more reflective surfaces for reflecting visible or infrared light to the at least one sensor. The fluid inlet port has at least one seal for sealing the fluid inlet port.

In accordance with another embodiment, a single-use disposable set connector may have a fluid inlet port configured for removable engagement with a connection port of a MUDS to establish a fluid connection therewith and a waste outlet port configured for removable engagement with a waste inlet port of the MUDS to establish a fluid connection therewith. A spacer may be provided to separate the fluid inlet port from the fluid outlet port. A locking mechanism may be configured for removably securing the connector to the MUDS. The locking mechanism may have a flexible tab that is deflectable between an engaged position and a disengaged position by deflecting at least a portion of the flexible tab. A patient fluid line may be connected, at a first end, to the fluid inlet port. A connector may be connected to a second end of the patient fluid line. Fluid flow through the patient fluid line may be unidirectional from the first end to the second end. The connector may be configured for removable fluid connection with the waste outlet port for delivering fluid to a patient.

In accordance with another embodiment, a method of delivering fluid using a single-use disposable set connector may include fluidly connecting a fluid inlet port of the single-use disposable set connector with a connection port of a multi-use disposable set (MUDS) and establishing a fluid communication between a waste outlet port of the single-use disposable set connector and a waste inlet port of the MUDS. The method may further include priming the single-use disposable set connector by delivering fluid from the fluid inlet port to the waste outlet port through a fluid line and disconnecting the fluid line from the waste outlet port. The method may further include delivering fluid from the fluid inlet port to a connector through the fluid line. In some embodiments, the method may include locking the single-use disposable set connector to the MUDS prior to priming the single-use disposable set connector.

These and other features and characteristics of single-use disposable set connectors, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

DETAILED DESCRIPTION

Figure 1:
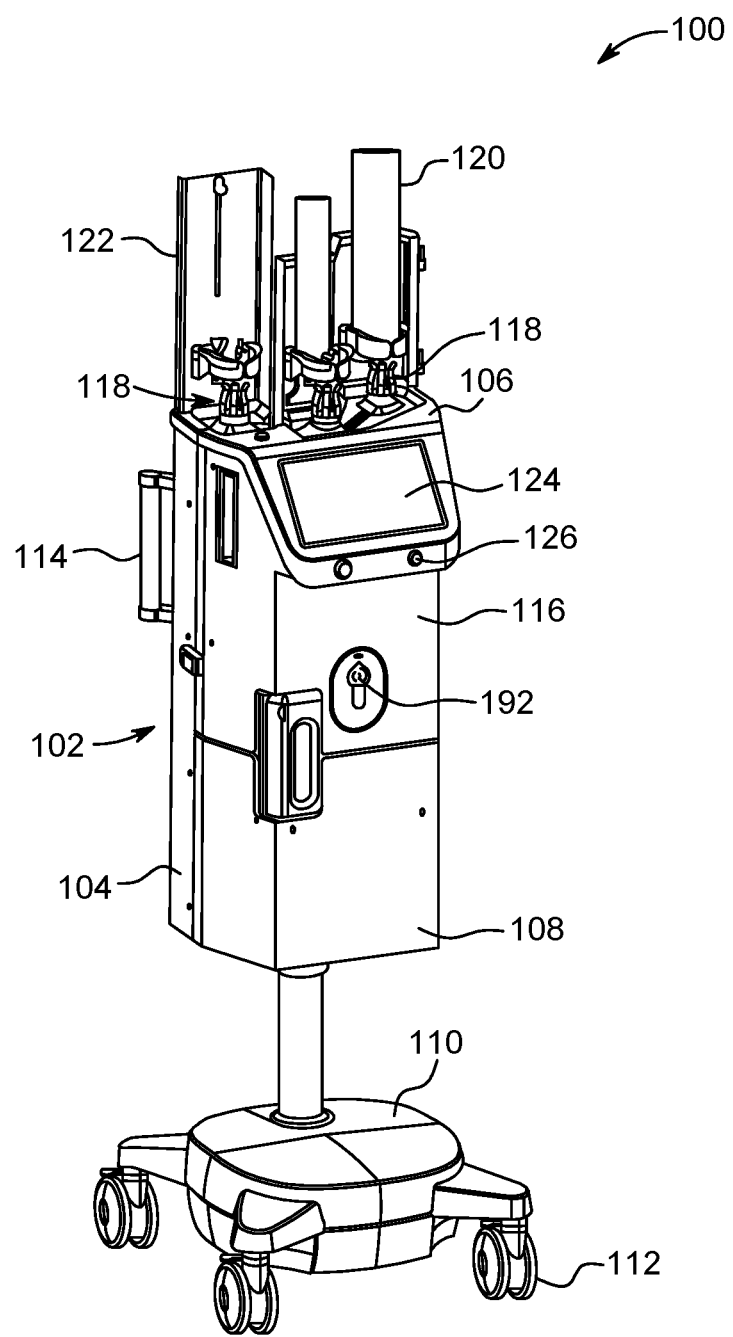
FIG. 1 is a perspective view of a multi-fluid delivery system, according to one embodiment.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a MUDS, the term "proximal" refers to a portion of a syringe nearest a piston element for delivering fluid from a syringe. When used in relation to a single-use disposable set connector, the term "distal" refers to a portion of a single-use disposable set SUDS connector nearest to a user when a single-use disposable set connector is oriented for connecting with a multi-fluid injector system. When used in relation to a syringe of a MUDS, the term "distal" refers to a portion of a syringe nearest to a delivery nozzle. When used in relation to a single-use disposable set connector, the term "proximal" refers to a portion of a single-use disposable set connector nearest to a multi-fluid injector system when a single-use disposable set connector is oriented for connecting with a multi-fluid injector system. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

Referring to the drawings in which like reference characters refer to like parts throughout the several views thereof, the present disclosure is generally directed to a multi-fluid medical injector/injection system 100 (hereinafter "fluid injector system 100") having a multi-use disposable set (MUDS) 130 configured for delivering fluid to a patient using a single-use disposable set (SUDS) connector. The fluid injector system 100 includes multiple components as individually described herein. Generally, the fluid injector system 100 has a powered injector administrator or device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein.

With reference to FIG. 1, the fluid injector system 100 includes an injector housing 102 having opposed lateral sides 104, a distal or upper end 106, and a proximal or lower end 108. In some embodiments, the housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other embodiments, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements 103 (shown in FIG. 2) associated with the fluid injector system 100 described herein. Such piston elements 103 may be reciprocally operable via electro-mechanical drive components such as a ball screw shaft driven by a motor, a voice coil actuator, a rack-and-pinion gear drive, a linear motor, and the like. In some embodiments, at least some of the mechanical drive components, electrical and power components, and control components may be provided on the base 110.

With continued reference to FIG. 1, the fluid injector system 100 has at least one door 116 that encloses at least some of the MUDS, the mechanical drive components, electrical and power components, and control components. The door 116 is desirably movable between an open position and a closed position (shown in FIG. 1). In some embodiments, the door 116 may be lockable.

The fluid injector system 100 further includes at least one bulk fluid connector 118 for connection with at least one bulk fluid source 120. In some embodiments, a plurality of bulk fluid connectors 118 may be provided. For example, as shown in FIG. 1, three bulk fluid connectors 118 may be provided in a side-by-side or other arrangement. In some embodiments, the at least one bulk fluid connector 118 may be a spike configured for removably connecting to the at least one bulk fluid source 120, such as a vial, a bottle, or a bag. The at least one bulk fluid connector 118 may have a reusable or non-reusable interface with each new bulk fluid source 120. The at least one bulk fluid connector 118 may be formed on the multi-use disposable set, as described herein. The at least one bulk fluid source 120 may be configured for receiving a medical fluid, such as saline, contrast solution, or other medical fluid, for delivery to the fluid injector system 100. The housing 102 may have at least one support member 122 for supporting the at least one bulk fluid source 120 once it is connected to the fluid injector system 100.

With continued reference to FIG. 1, the fluid injector system 100 includes one or more user interfaces 124, such as a graphical user interface (GUI) display window. The user interface 124 may display information pertinent to a fluid injection procedure involving fluid injector system 100, such as current flow rate, fluid pressure, and volume remaining in the at least one bulk fluid source 120 connected to the fluid injector system 100 and may be a touch screen GUI that allows an operator to input commands and/or data for operation of fluid injector system 100. While the user interface 124 is shown on the injector housing 102, such user interface 124 may also in the form of a remote display that is wired or wirelessly linked to the housing 102 and control and mechanical elements of fluid injector system 100. In some embodiments, the user interface 124 may be a tablet computer that is detachably connected to the housing 102 and is in wired or wirelessly linked communication with the housing 102. Additionally, the fluid injector system 100 and/or user interface 124 may include at least one control button 126 for tactile operation by an attendant operator of the fluid injector system 100. In certain embodiments, the at least one control button may be part of a keyboard for inputting commands and/or data by the operator. The at least one control button 126 may be hard-wired to the electronic control device(s) associated with the fluid injector system 100 to provide direct input to the electronic control device (s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) acknowledging that a multi-use disposable set has been loaded or unloaded; (2) locking/unlocking of the multi-use disposable set; (3) filling/purging of the fluid injector system 100; (4) inputting information and/or data related to the patient and/or injection procedure, and (5) initiating/stopping an injection procedure. The user interface 124 and/or any electronic processing units associated with the fluid injector system 100 may be wired or wirelessly connected to an operation and/or data storage system such as a hospital network system.

Figure 2:
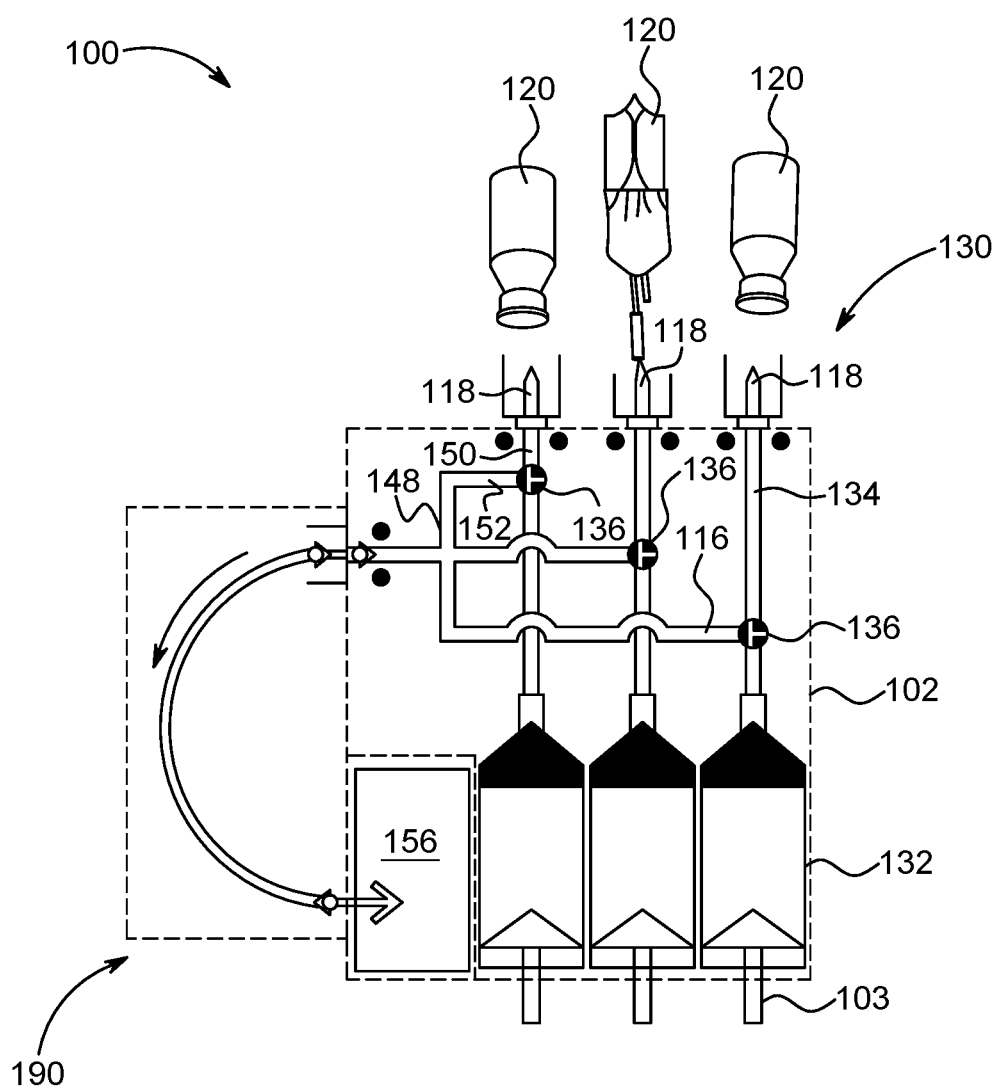
FIG. 2 is schematic view of various fluid paths within the multi-fluid delivery system of FIG. 1.

With reference to FIG. 2, the fluid injector system 100 includes a MUDS 130 that is removably connected to the fluid injector system 100 for delivering one or more fluids from the one or more bulk fluid sources 120 to the patient. The MUDS 130 may include one or more syringes or pumps 132. In some embodiments, the number of syringes 132 may correspond to the number of bulk fluid sources 120. For example, with reference to FIG. 2, the MUDS 130 has three syringes 132 in a side-by-side arrangement such that each syringe 132 is fluidly connectable to one or more of the bulk fluid sources 120. In some embodiments, one or two bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118. In some embodiments, the bulk fluid connector 118 may be provided directly on the MUDS 130.

With further reference to FIG. 2, the MUDS 130 is removably connectable to the housing 102 of the fluid injector system 100. As will be appreciated by one having ordinary skill in the art, it may be desirable to construct at least a portion of the MUDS 130 from a clear medical grade plastic in order to facilitate visual verification that a fluid connection has been established with the fluid injector system 100. Visual verification is also desirable for confirming that no air bubbles are present within various fluid connections. Alternatively, at least a portion of the MUDS 130 and/or door 116 may include windows (not shown) for visualization of the connection between various components. Various optical sensors (not shown) may also be provided to detect and verify the connections. Additionally, various lighting elements (not shown), such as light emitting diodes (LEDs), may be provided to actuate one or more optical sensors and indicate that a suitable connection has been established between the various components.

With specific reference to FIG. 2, a schematic view of various fluid paths of the fluid injector system 100 is provided. The MUDS 130 may include one or more valves 136, such as stopcock valves, for controlling which medical fluid or combinations of medical fluids are withdrawn from the multi-dose bulk fluid source 120 and/or are delivered to a patient through each syringe 132. In some embodiments, the one or more valves 136 may be provided on the distal end 140 of the plurality of syringes 132 or on the manifold 148. The manifold 148 may in fluid communication via valves 136 and/or syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the one or more syringes 132, or it may be delivered from the one or more syringes 132. In a first position, such as during the filling of the syringes 132, the one or more valves 136 are oriented such that fluid flows from the bulk fluid source 120 into the desired syringe 132 through a fluid inlet line 150, such as MUDS fluid path. During the filling procedure, the one or more valves 136 are positioned such that fluid flow through one or more fluid outlet lines 152 or manifold 148 is blocked. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked. The one or more valves 136, fluid inlet lines 150, and/or fluid outlet lines 152 may be integrated into the manifold 148. The one or more valves 136 may be selectively positioned to the first or second position by manual or automatic handling. For example, the operator may position the one or more valves 136 into the desired position for filling or fluid delivery. In other embodiments, at least a portion of the fluid injector system 100 is operable for automatically positioning the one or more valves 136 into a desired position for filling or fluid delivery based on input by the operator, as described herein.

With continued reference to FIG. 2, in some embodiments, the fluid outlet line 152 may also be connected to a waste reservoir 156 on the fluid injector system 100. The waste reservoir 156 is desirably separate from the syringes 132 to prevent contamination. In some embodiments, the waste reservoir 156 is configured to receive waste fluid expelled from the syringes 132 during, for example, a priming operation. The waste reservoir 156 may be removable from the housing 102 in order to dispose of the contents of the waste reservoir 156. In other embodiments, the waste reservoir 156 may have a draining port (not shown) for emptying the contents of the waste reservoir 156 without removing the waste reservoir 156 from the housing 102. In some embodiments, the waste reservoir 156 is provided as a separate component from the MUDS 130.

Having generally described the components of the fluid injector system 100 and the MUDS 130, the structure and method of use of a single-use disposable set 190 (SUDS) and its interaction with MUDS 130 will now be described.

Figure 3A:
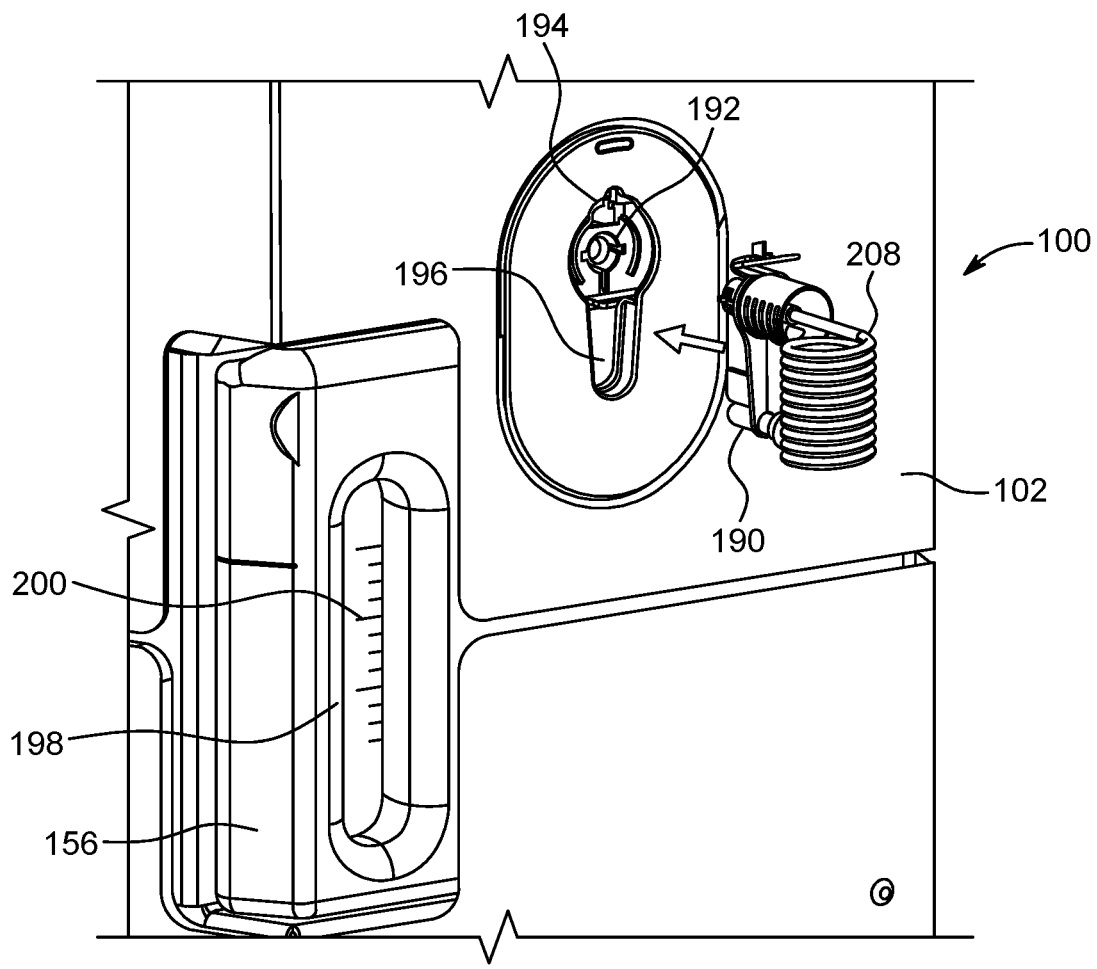
FIG. 3A is a perspective view of a connection interface prior to connecting a single-use disposable set connector with a multi-fluid delivery system.
Figure 3B:
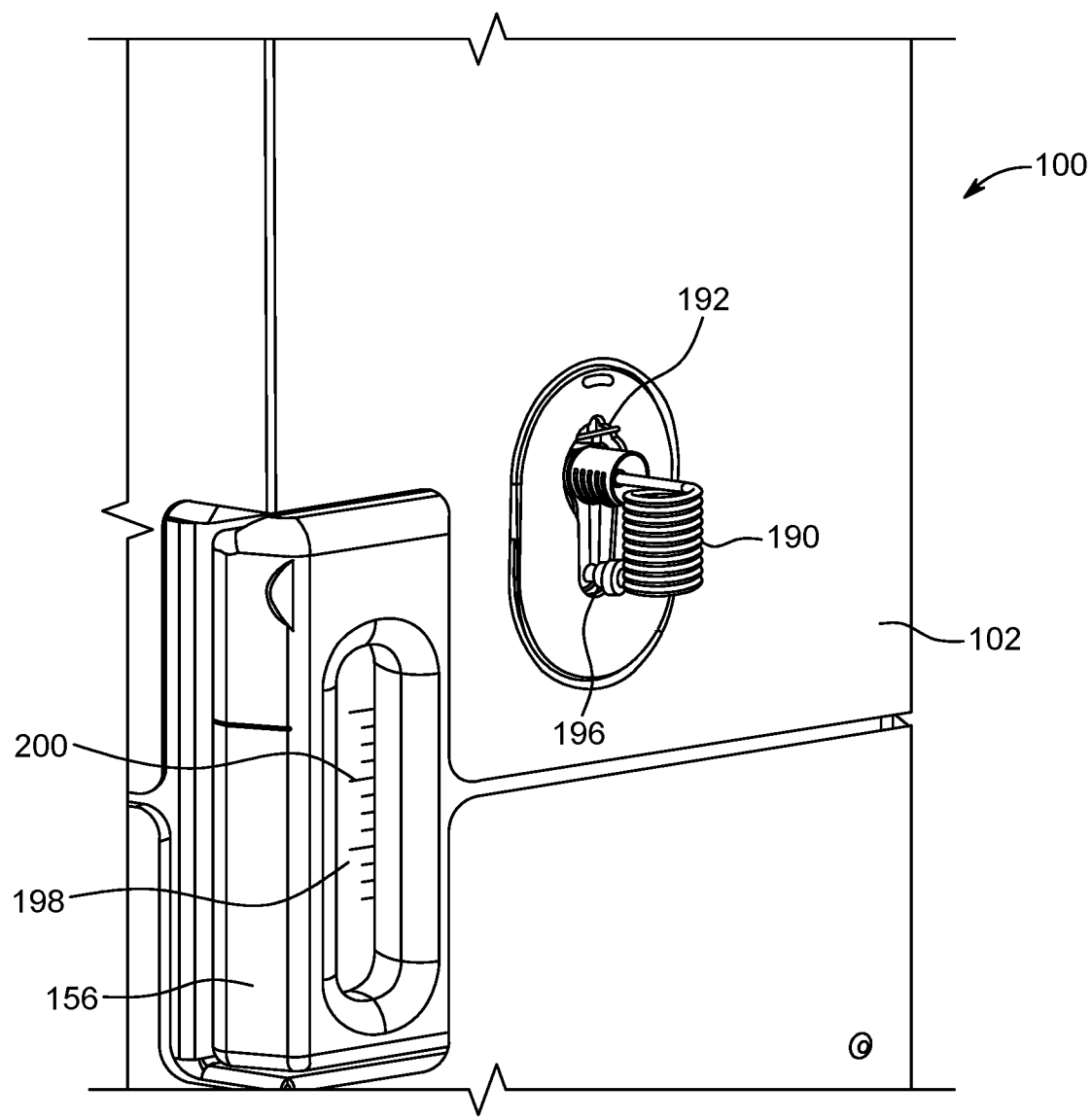
FIG. 3B is a perspective view of the connection interface of FIG. 3A showing the single-use disposable set connector connected with the multi-fluid delivery system.

With reference to FIGS. 3A and 3B, the fluid injector system 100 has a connection port 192 that is configured to form a releasable fluid connection with at least a portion of the SUDS 190. In some embodiments, the connection port 192 may be formed on the MUDS 130. The connection port 192 may be shielded by at least a portion of the housing 102 of the fluid injector system 100. For example, recessing the connection port 192 within the interior of the housing 102 may preserve the sterility of the connection port 192 by preventing or limiting a user or patient from touching and contaminating the portions of the connection port 192 that contact the fluid to be injected to the patient. In some embodiments, the connection port 192 is recessed within an opening 194 formed on the housing 102 of the fluid injector system 100, or the connection port 192 may have a shielding structure (not shown) that surrounds at least a portion of the connection port 192. In other embodiments, the connection port 192 may be formed directly on the housing 102 and connected to the MUDS 130 by a fluid path (not shown). As described herein, the SUDS 190 may be connected to the connection port 192, formed on at least a portion of the MUDS 130 and/or the housing 102. Desirably, the connection between the SUDS 190 and the connection port 192 is a releasable connection to allow the SUDS 190 to be selectively disconnected from the connection port 192 (FIG. 3A) and connected to the connection port 192 (FIG. 3B). In some embodiments, the SUDS 190 may be disconnected from the connection port 192 and disposed after each fluid delivery procedure and a new SUDS 190 may be connected to the connection port 192 for a subsequent fluid delivery procedure.

With continued reference to FIGS. 3A and 3B, a waste inlet port 196 may be provided separately from the connection port 192. The waste inlet port 196 is in fluid communication with the waste reservoir 156. In some embodiments, the waste reservoir 156 is provided separately from the SUDS 190 such that the fluid from the waste inlet port 196 can be delivered to the waste reservoir 156. At least a portion of the SUDS 190 may be releasably connected to or associated with the waste inlet port 196 for introducing waste fluid into the waste reservoir 156 during, for example, a priming operation that expels air from the SUDS 190. The waste reservoir 156 may have a viewing window 198 with indicia 200, such as graduated markings, that indicate the fill level of the waste reservoir 156.

Figure 4A:
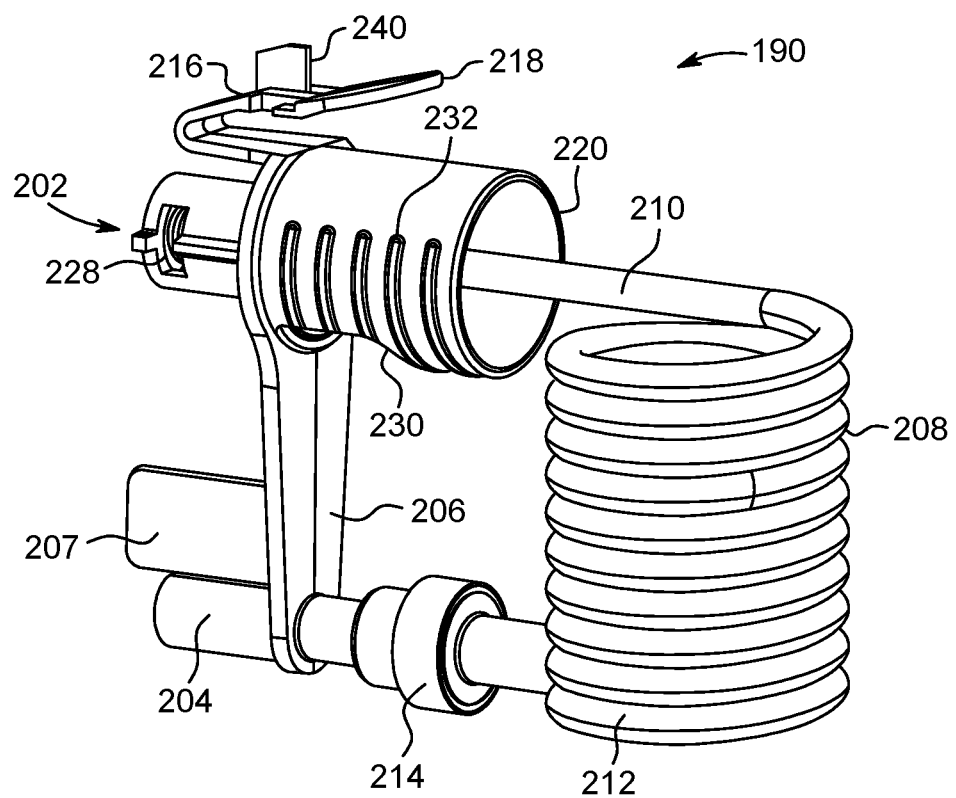
FIG. 4A is a perspective view of a single-use disposable set connector in accordance with one embodiment.
Figure 4B:
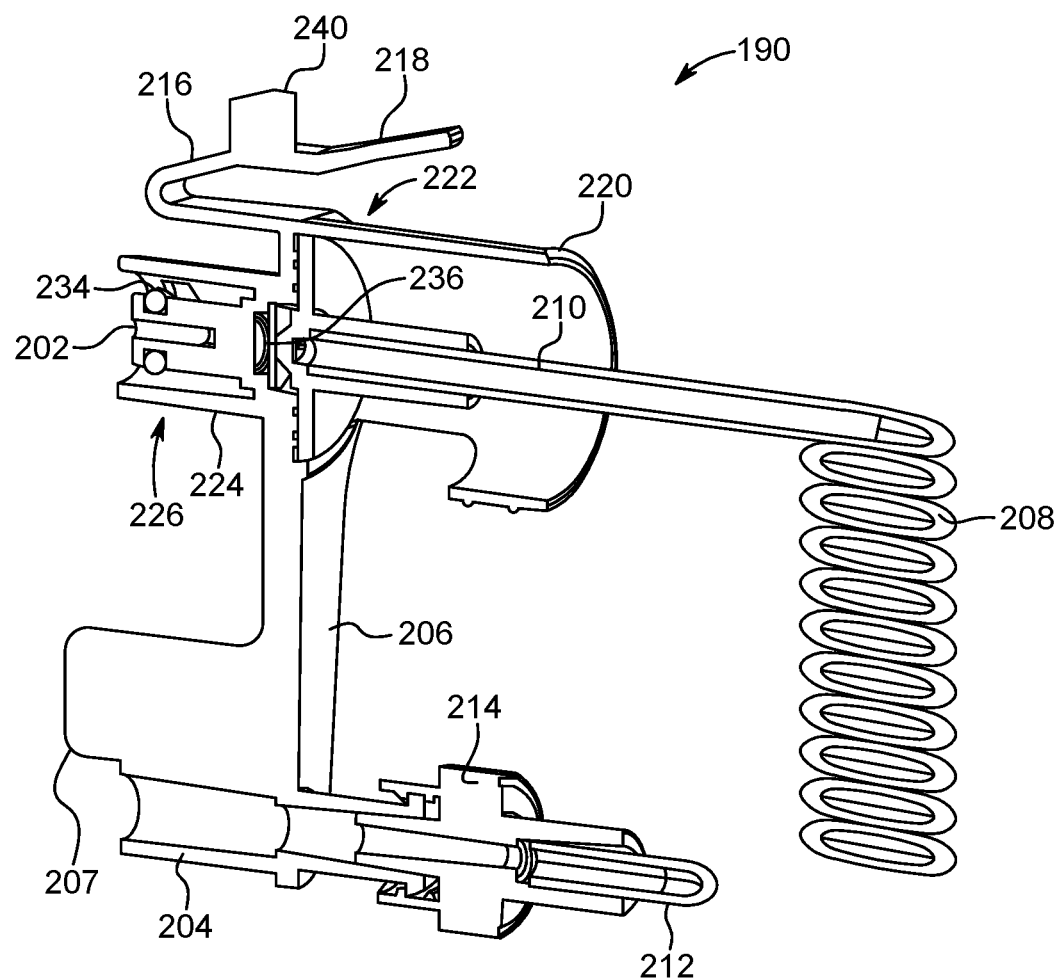
FIG. 4B is a cross-sectional view of the single-use disposable set connector shown in FIG. 4A.

With reference to FIG. 4A, the SUDS 190 has a fluid inlet port 202 that is configured for releasable connection with the connection port 192 (shown in FIG. 3A). The fluid inlet port 202 receives fluid delivered from the fluid injector system 100. The fluid inlet port 202 is desirably a hollow, tubular structure, as shown in FIG. 4B. The SUDS 190 further has a waste outlet port 204 that is configured for releasable connection or association with the waste inlet port 196 (shown in FIG. 3A). The waste outlet port 204 receives waste fluid and delivers such waste fluid to the waste reservoir 156 during, for example, a priming operation of the SUDS 190. The waste outlet port 204 is desirably a hollow, tubular structure, as shown in FIG. 4B. The waste outlet port 204 may be connected to, inserted into, or located in the waste inlet port 196 so that the waste fluid may flow through the waste inlet port 196 and continue into waste reservoir 156. The fluid inlet port 202 and the waste outlet port 204 may be spaced apart from each other by a spacer 206. In some embodiments, the spacer 206 is dimensioned to position the fluid inlet port 202 and the waste outlet port 204 for alignment with the connection port 192 and the waste inlet port 196, respectively. It is noted that the SUDS 190 is shown in FIG. 4A in a state after removal from packaging (not shown). Prior to use, the SUDS 190 is desirably packaged in a pre-sterilized, sealed package that protects the SUDS 190 from contamination with air or surface-borne contaminants. Alternatively, the sealed package and SUDS 190 may be sterilized after packaging.

The SUDS 190 desirably has an asymmetrical structure, so that the user can only attach the SUDS 190 to the MUDS 130 in one orientation. In this manner, the user is prevented from attaching the fluid inlet port 202 to the waste inlet port 196. In some embodiments, a fin 207 may be provided on at least a portion of the SUDS 190 to prevent erroneous insertion of the SUDS 190 in the connection port 192. In certain embodiments, the fin 207 may be formed on the spacer 206 proximate to the waste outlet port 204. In this manner, the fin 207 may interfere with the incorrect insertion of the SUDS 190 into the connection port 192. Structures and shapes other than fin 207 may be used to prevent erroneous insertion of the SUDS 190 into connection port 192, In some embodiments, tubing 208 may be connected at its proximal end 210 to the fluid inlet port 202. The tubing 208 is configured to deliver fluid received from the fluid inlet port 202. The distal end 212 of the tubing 208 may have a connector 214 that is configured for connection with the waste outlet port 204 or a fluid path connected to the patient (not shown). The tubing 208 may be made from a flexible material, such as a medical grade plastic material, that allows the tubing 208 to be coiled. The connector 214 may be a luer-lock connector (either a male luer-lock connector or a female luer-lock connector depending on the desired application) or other medical connector configuration. In some embodiments, the connector 214 may have a one-way valve to prevent backflow of fluid. Alternatively, a one-way valve may be located elsewhere in the SUDS 190 between fluid inlet port 202 and connector 214.

With continued reference to FIG. 4A, the SUDS 190 may have a locking tab 216 that is configured for selectively locking the SUDS 190 with the fluid injector system 100 depending on the engagement of the locking tab 216 with at least a portion of the fluid injector system 100. In some embodiments, the locking tab 216 may be a flexible tab that is deflectable between an engaged position and a disengaged position by deflecting at least a portion of the locking tab 216. The locking tab 216 may have a pressing surface 218 that, when pressed, causes the locking tab 216 to be deflected from the engaged position to the disengaged position for insertion and removal of the SUDS 190 from the fluid injector system 100. In some embodiments, the locking tab 216 may be configured for releasable locking engagement with a receiving slot 217 on the MUDS 130 (shown in FIG. 4C).

With reference to FIG. 4B, the SUDS 190 may have a first annular skirt 224 extending circumferentially around a proximal end 226 of the fluid inlet port 202 and a second annular skirt 220 extending circumferentially around a distal end 222 of the fluid inlet port 202. The first and second annular skirts 224, 220 surround the fluid inlet port 202 to prevent inadvertent contact and contamination. The first annular skirt 224 may have one or more recesses 228 (shown in FIG. 4A) extending through a sidewall thereof.

The one or more recesses 228 may provide a locking interface with a corresponding locking element (not shown) on the fluid injector system 100. The second annular skirt 220 may have at least one indentation 230 (shown in FIG. 4A) to facilitate grasping and handling of the SUDS 190. In some embodiments, the second annular skirt 220 may have a textured surface having one or more ribs 232 (shown in FIG. 4A) to facilitate gripping and handling of the SUDS 190.

With continued reference to FIG. 4B, at least one annular seal 234 may be provided around the proximal end 226 of the fluid inlet port 202. The at least one annular seal 234 may seal the fluid inlet port 202 to prevent fluid from leaking through the SUDS 190. The at least one annular seal 234 may provide a fluid seal between the SUDS 190 and the MUDS 130 when they are fluidly connected with one another to allow fluid to flow from the MUDS 130 to the SUDS 190 without leaking. A one-way valve 236 may be provided within a lumen of the fluid inlet port 202 to prevent fluid from flowing in a reverse direction from the SUDS 190 into the MUDS 130.

Figure 4C:
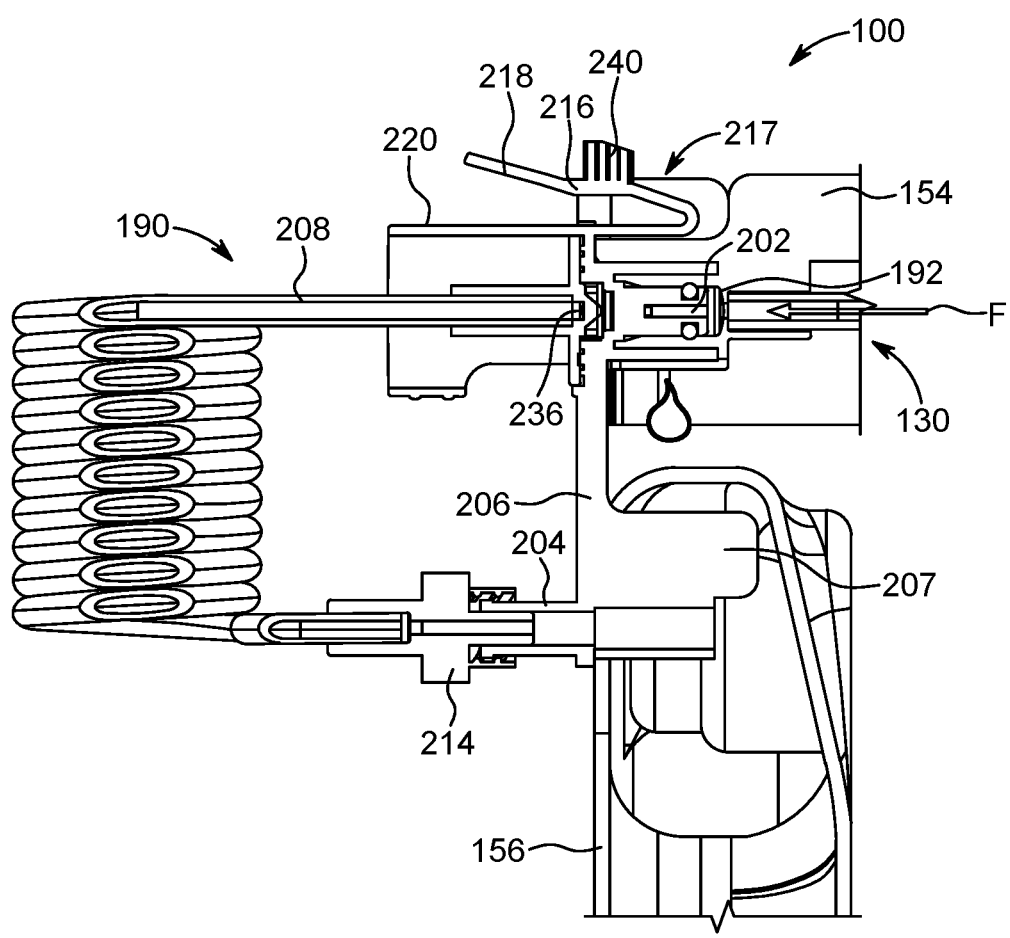
FIG. 4C is a cross-sectional view of the single-use disposable set connector shown in FIG. 4A connected to a port of a multi-fluid delivery system.

With reference to FIG. 4C, the SUDS 190 shown in FIG. 4A is shown connected to the fluid injector system 100. While FIG. 4C illustrates the connection port 192 formed on the MUDS 130, in other embodiments, the connection port 192 may be formed on a portion of the housing 102 (shown in FIG. 1). The fluid inlet port 202 of the SUDS 190 is connected to the connection port 192 to establish a fluid path in a direction of arrow F shown in FIG. 4C. Fluid passing through the fluid inlet port 202 flows through the one-way valve 236 and into tubing 208. Any fluid that may drip from the interface between the fluid inlet port 202 and the connection port 192 is collected in the waste reservoir 156. The waste reservoir 156 may be shaped to collect any fluid that may drip from the SUDS 190 when it is removed from the MUDS 130. Additionally, when the SUDS 190 is connected to the connection port 192, the outlet of the waste outlet port 204 is positioned within the waste inlet port 196 such that waste fluid from the tubing 208 may be discharged into the waste reservoir 156. The spacer 206 may define an insertion stop surface to define the depth of insertion of the SUDS 190 into the connection port 192.

Figure 5A:
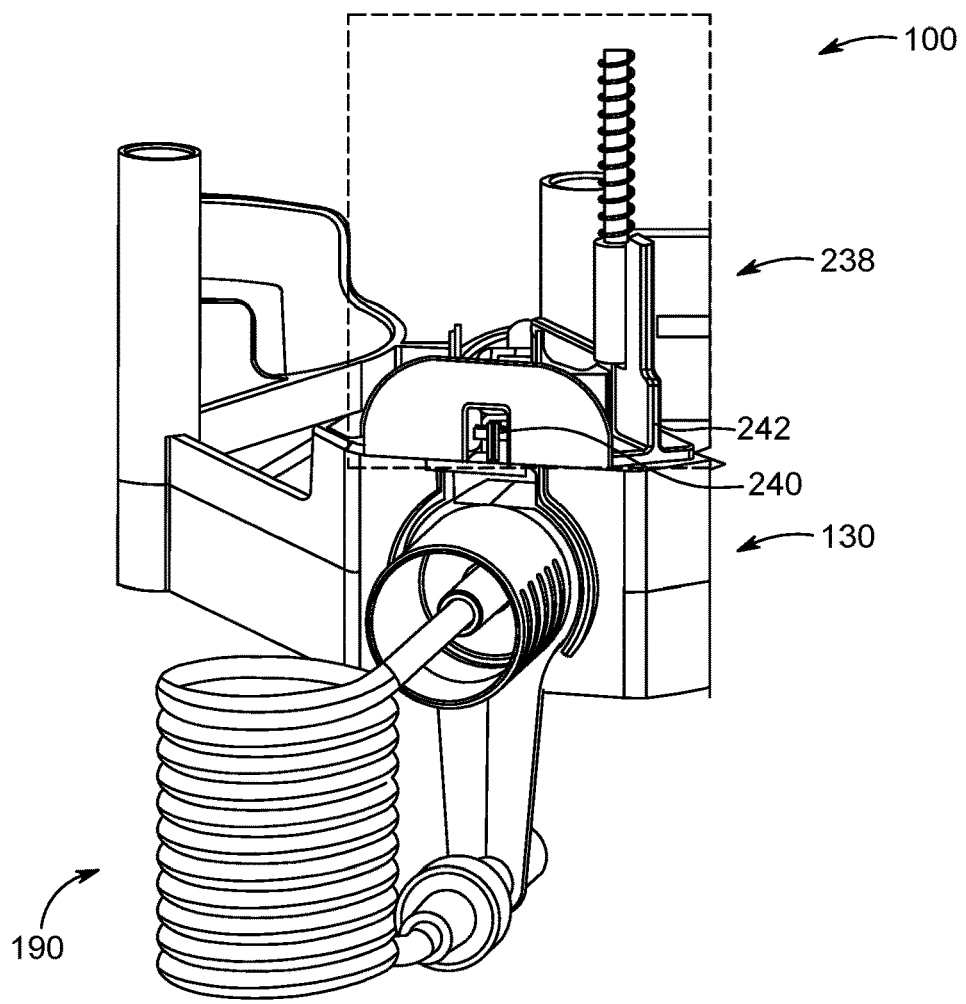
FIG. 5A is a perspective view of the single-use disposable set connector shown in FIG. 4C with a portion of the multi-fluid delivery system and the MUDS cut away.
Figure 5B:
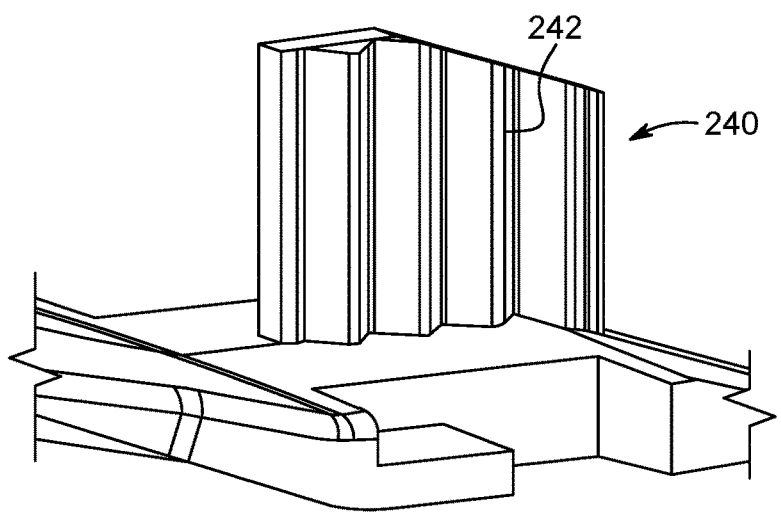
FIG. 5B is a detailed perspective view of a sensor rib of the single-use disposable set connector shown in FIG. 5A.

With reference to FIG. 5A, the fluid injector system 100 may have a sensor system 238 adapted to identify when the SUDS 190 is in fluid communication with the MUDS 130. The sensor system 238 may include at least one sensing element, such as a sensor fin 240, on the SUDS 190 and a corresponding sensor 242 on the fluid injector system 100 or MUDS 130. The sensor 242 may be configured to detect the presence and absence of the at least one sensor fin 240, or other sensing element. In some embodiments, the sensing element, such as the at least one sensor fin 240 is formed on the locking tab 216 of the SUDS 190, such as shown in FIG. 4A. In other embodiments, the sensing element, such as the at least one sensor fin 240 may be formed on any portion of the SUDS 190. The sensor 242 may be an optical sensor that is seated and secured within a respective mount formed on the housing 102 of the fluid injector system 100. As will be appreciated by those versed in the field of powered medical fluid injectors, the sensor 242 may be electronically coupled to an electronic control device used to discretely control operation of the fluid injector system, such as the operation of the one or more piston elements, based, at least in part, on input from the sensor 242. The sensing element, such as the sensor fin 240 may have one or more reflective surfaces that reflect visible or infrared light to be detected by the sensor 242. In other embodiments, mechanical interaction between the sensing element and the sensor 242 may be used.

In some embodiments, the SUDS 190 may further include reuse prevention features (not shown). For example, the SUDS 190 may include one or more breakable sensor elements, tabs, or structures that fold or break when the SUDS 190 is removed from the MUDS 130. Absence of these features may prevent reinsertion and reuse of the SUDS 190 after removal. In this manner, it can be assured that the SUDS 190 is only used for one fluid delivery procedure.

Having generally described the components of the fluid injector system 100, the MUDS 130, and the SUDS 190, a method of operation of using the SUDS 190 will now be described in detail. In use, a medical technician or user removes the disposable SUDS 190 from its packaging (not shown) and inserts the fluid inlet port 202 into the connection port 192 on the MUDS 130. As described above, the SUDS 190 must be inserted in the correct orientation, such that the fluid inlet port 202 is aligned for connection with the connection port 192, and the waste outlet port 204 is aligned for connection with the waste inlet port 196. The SUDS 190 may be secured to the MUDS 130 by inserting the locking tab 216 into the receiving slot 217 on the MUDS 130. Once the SUDS 190 is securely connected to the MUDS 130, for example as sensed by the sensor 242, the fluid injector system 100 (shown in FIG. 1) draws fluid into one or more of the plurality of syringes 132 of the MUDS 130 and performs an automatic priming operation for removing air from the MUDS 130 and the SUDS 190. During such priming operation, fluid from the MUDS 130 is injected through the connection port 192 and into the tubing 208 of the SUDS 190. The fluid flows through the tubing 208 and through the waste outlet port 204 and into the waste reservoir 156. Once the automatic priming operation is completed, the medical technician disconnects the connector 214 from the waste outlet port 204. The connector 214 may then be connected to the patient through a catheter, vascular access device, needle, or additional fluid path set to facilitate fluid delivery to the patient. Once the fluid delivery is completed, the SUDS 190 is disconnected from the patient and the MUDS 130 by disengaging the locking tab 216 of the SUDS 190 from the receiving slot 217 on the MUDS 130. The medical technician may then dispose of the SUDS 190. In certain embodiments, removing the SUDS 190 from the MUDS 130 causes reuse prevention features (not shown) to activate, thereby preventing reinsertion and reuse of the SUDS 190.

Figure 6:
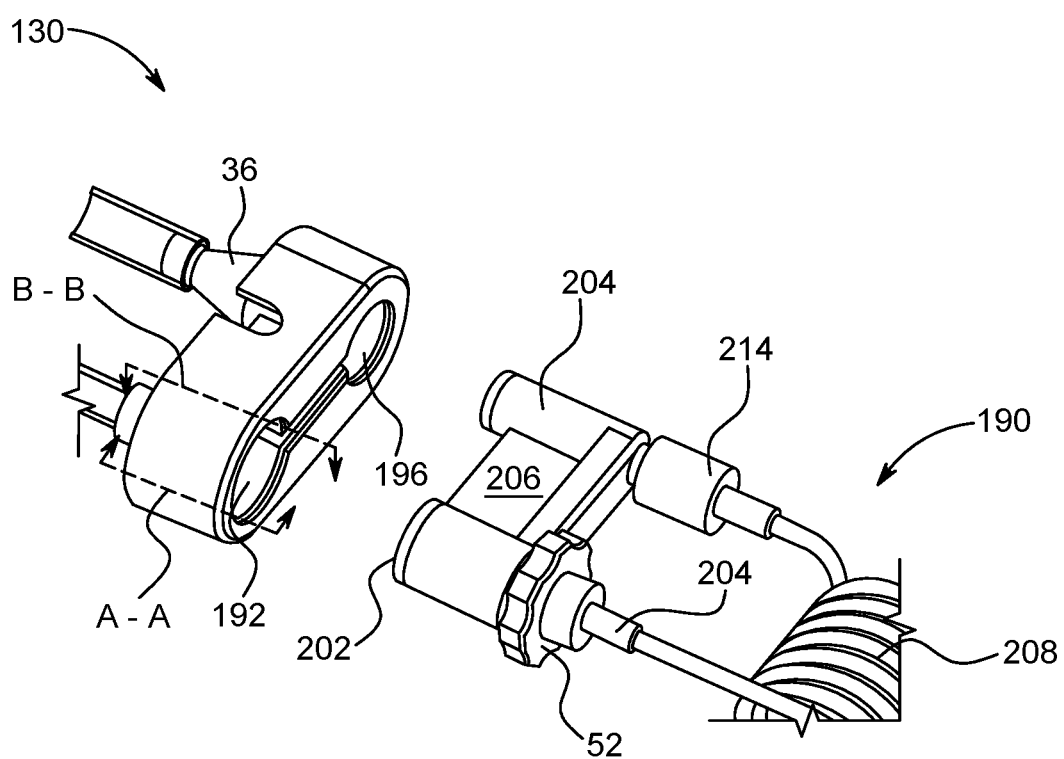
FIG. 6 is a perspective view of a single-use disposable set connector in accordance with another embodiment.
Figure 7A:
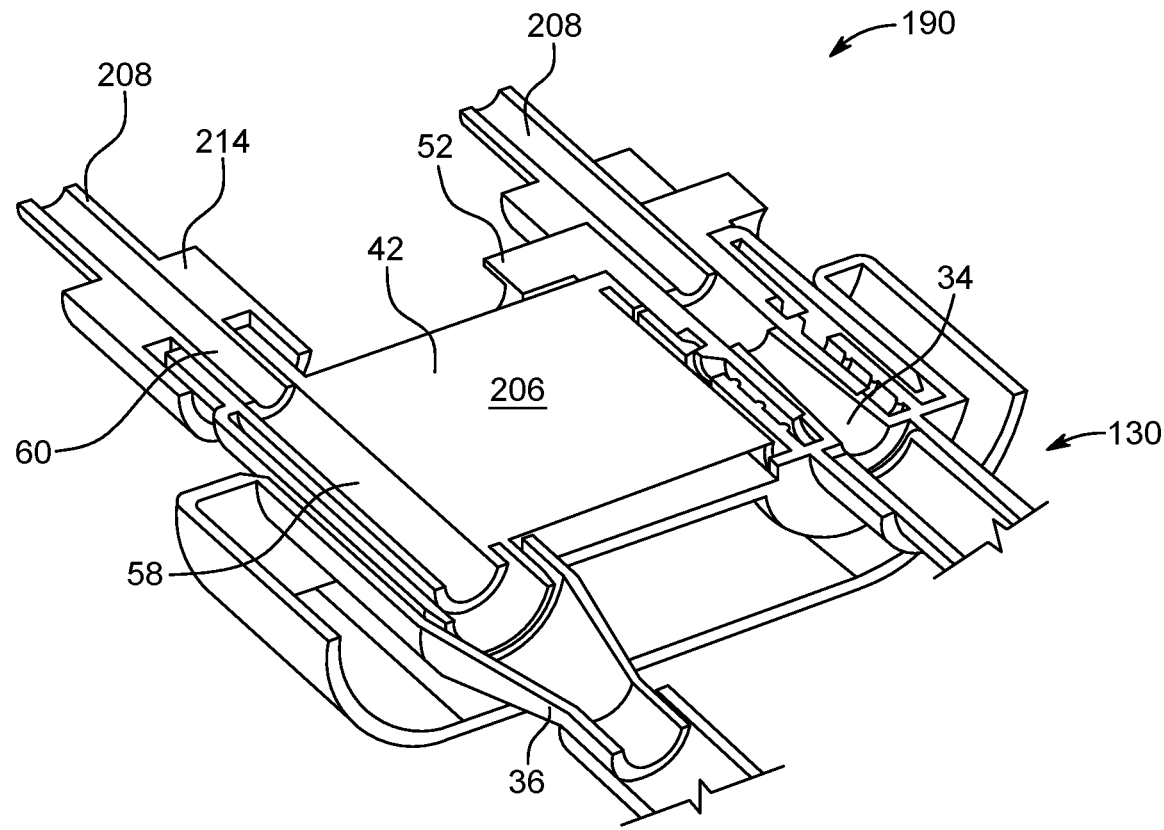
FIG. 7A is an enlarged cross-sectional view of the single-use disposable set connector shown in FIG. 6, taken along line A-A.
Figure 7B:
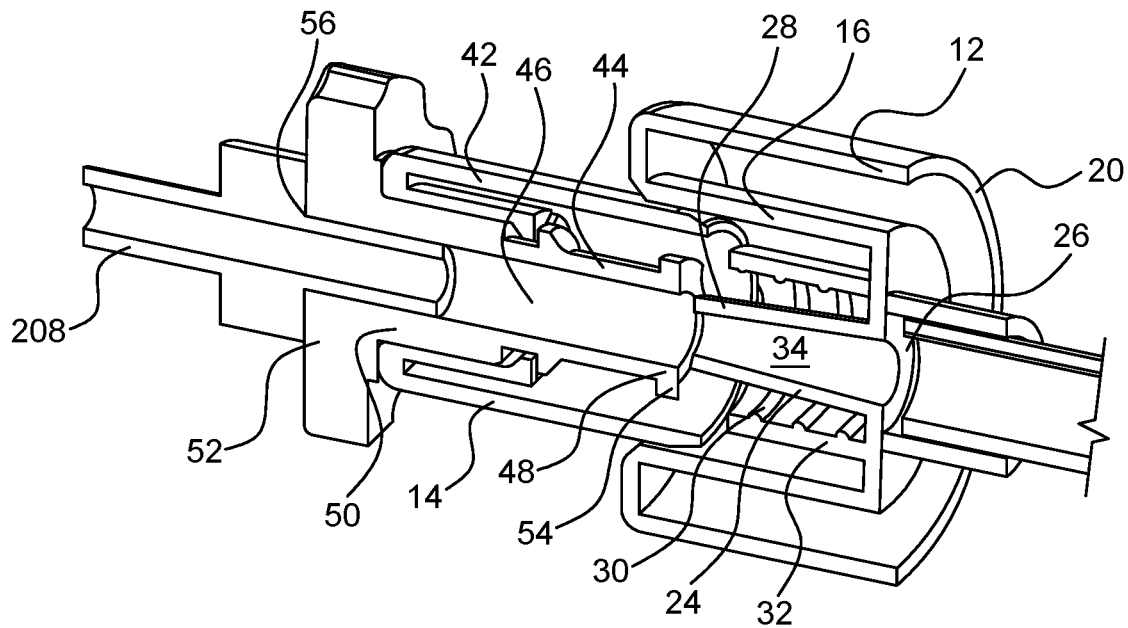
FIG. 7B is an enlarged cross-sectional view of the single-use disposable set connector shown in FIG. 6, taken along line B-B.

With reference to FIG. 6, a connection interface between the SUDS 190 and the MUDS 130 is shown in accordance with another embodiment. The MUDS 130 has a connection port 192 that may be configured as a hollow, tubular structure having a luer lock connector 24 (either a male luer lock connector or a female luer lock connector depending on the desired application), extending from a distal end of the port 192 into an interior of the port 192. Accordingly, the proximal opening of the luer lock connector 24 is recessed within the interior of the port 192. The luer lock connector 24 may include screw threads 30 (shown in FIG. 7B) for securing the MUDS 130 to the SUDS 190. For example, the screw threads 30 may be positioned on an outer shroud 32 surrounding the luer lock connector 24, as shown in FIGS. 7A and 7B. Screw threads 30 may also be positioned on the luer lock connector 24 itself. The luer lock connector 24 defines a fluid passageway 34 (shown in FIG. 7B) extending therethrough, from the proximal end of the connection port 192 to the distal opening thereof. While the connection port 192 is depicted as including a luer lock connector 24, other styles of connectors, including, but not limited to, clip-in connectors, bayonet connectors, press fit connectors, and the like, may be used within the scope of the present disclosure. Additionally, in certain embodiments, the connector 24 for the connection port 192 is desirably a non-standard connector (e.g. a connector with an unusual size or shape) so that connectors produced by third parties cannot be attached.

The MUDS 130 has a waste inlet port 196 (shown in FIG. 6) that may also be configured as a hollow, tubular structure. The waste inlet port 196 includes a tapered distal nozzle 36 attached to a fluid conduit, such as flexible tubing 208, formed from a medical grade polymer, that connects the waste inlet port 196 to the waste reservoir 156 (shown in FIG. 2).

With reference again to FIG. 6, as described in detail herein, the MUDS 130 is adapted for connecting to the SUDS 190, which is disposed of after a single use. It is noted that the SUDS 190 is shown in FIG. 6 in a state after removal from packaging (not shown). Prior to use, the SUDS 190 is desirably packaged in a pre-sterilized, sealed package that protects the SUDS 190 from contamination with air or surface-borne contaminants.

The SUDS 190 may have two or more ports, corresponding to the connection port 192 and waste inlet port 196 of the MUDS 130. For convenience, the ports of the SUDS 190 are equivalent to the fluid inlet port 202 and the waste outlet port 204 of the SUDS 190 described with reference to FIGS. 4A-4B. The ports 202, 204 may be provided in an enclosure 42 suitable for receipt within the housing 20 of the MUDS 130, as shown in FIG. 7B. The enclosure 42 desirably has an asymmetrical structure, so that the user can only attach the SUDS 190 to the MUDS 130 in one orientation only. Thus, for example, the user is prevented from attaching the connection port 192 of the MUDS 130 to the SUDS 190 waste outlet port 204. The ports 202, 204 and enclosure 42 of the SUDS 190 may be made from a material suitable for medical applications, such as medical grade plastic. The tubing 208 of the SUDS 190 is connected between the proximal end of the fluid inlet port 202 and the end of the waste outlet port 204 through check valves. The tubing 208 may be provided in a wound or coiled configuration for easy packaging and maneuverability.

With reference to FIGS. 7A and 7B, the SUDS 190 fluid inlet port 202 is a hollow, tubular structure configured for insertion in the connection port 192 of the MUDS 130. The SUDS 190 fluid inlet port 202 includes a tubular conduit, such as a luer lock connector 44, defining a fluid passageway 46 extending from a proximal end of the port 202, located adjacent to the MUDS 130, and the distal end of the port 204, connected to the tubing 208. The luer lock connector 44 is adapted to connect to the luer lock connector 24 of the MUDS 130. When securely connected, the connection port 192 of the MUDS 130 is in fluid communication with the fluid inlet port 202 of the SUDS 190. The luer lock connector 44 may include a thumbwheel 52 for securing the connection port 192 of the MUDS 130 to the SUDS 190 fluid inlet port 202. The thumbwheel 52 may be integrally formed with the luer lock connector 44 or may be a separate structure fixedly connected to the luer lock connector 44 by conventional means. The thumbwheel 52 rotates the luer lock connector 44 causing tabs 54, extending therefrom, to engage the corresponding screw threads 30 in the connection port 192. The tubing 208 is connected to the fluid inlet port 202 through an opening 56 on the thumbwheel 52, such that a continuous fluid connection is established from the MUDS 130 to the tubing 208.

With continued reference to FIGS. 7A and 7B, the SUDS 190 also includes the SUDS 190 waste outlet port 204. The SUDS waste outlet port 204 has a fluid passageway 58, defined by a tubular conduit 60, extending between the waste inlet port 196 of the MUDS 130, and the tubing 208. The tubing 208 may not be directly connected to the waste inlet port 196 of the MUDS 130. Instead, the tubular conduit 60 of the SUDS 190 may separate the tubing 208 from the MUDS 130, thereby ensuring that the tubing 208 and the connector 214 are isolated from the waste inlet port 196 of the MUDS 130. The tubular conduit 60 may be recessed from the waste inlet port 196 of the MUDS 130 by a portion of the single-use connector enclosure 42, to reduce the likelihood of contamination. The tubular conduit 60 may also be angled, relative to the horizontal, to facilitate fluid flow through the SUDS 190 waste outlet port 204 and into the waste inlet port 196 of the MUDS 130. In some embodiments, the SUDS 190 may further include reuse prevention features (not shown). For example, the SUDS 190 may include breakable tabs or structures that fold or break when the SUDS 190 is removed from the MUDS 130. In this manner, it can be assured that the SUDS 190 is only used for one fluid delivery procedure.

Figure 8A:
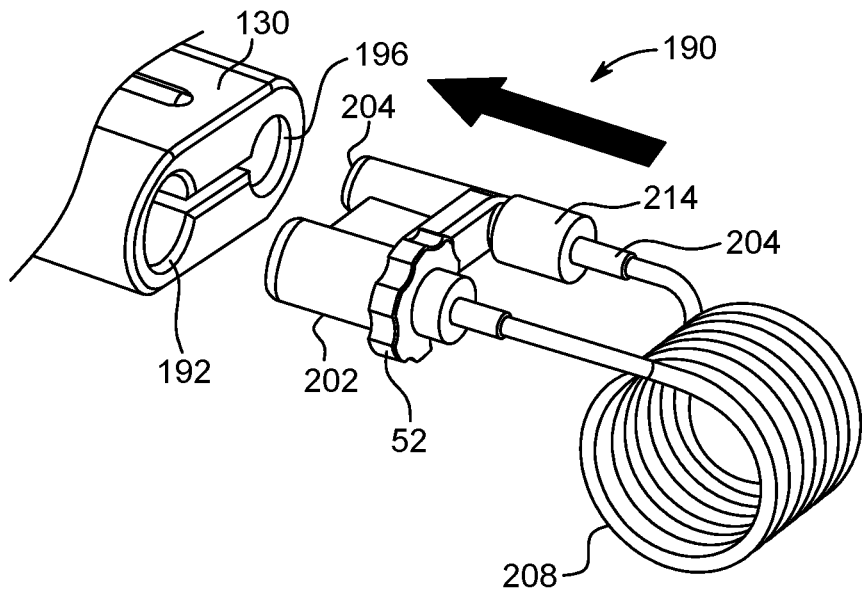
FIGS. 8A-8F are perspective views of various stages of connecting a single-use disposable set connector to a MUDS connector.
Figure 8B:
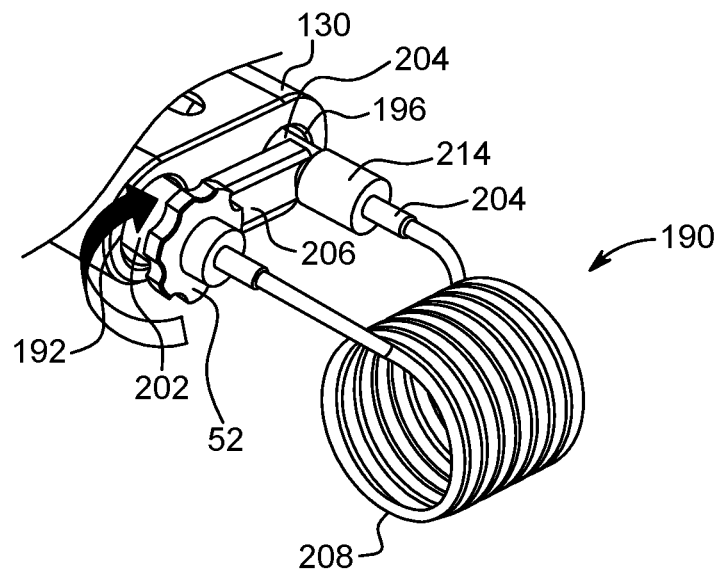
Figure 8C:
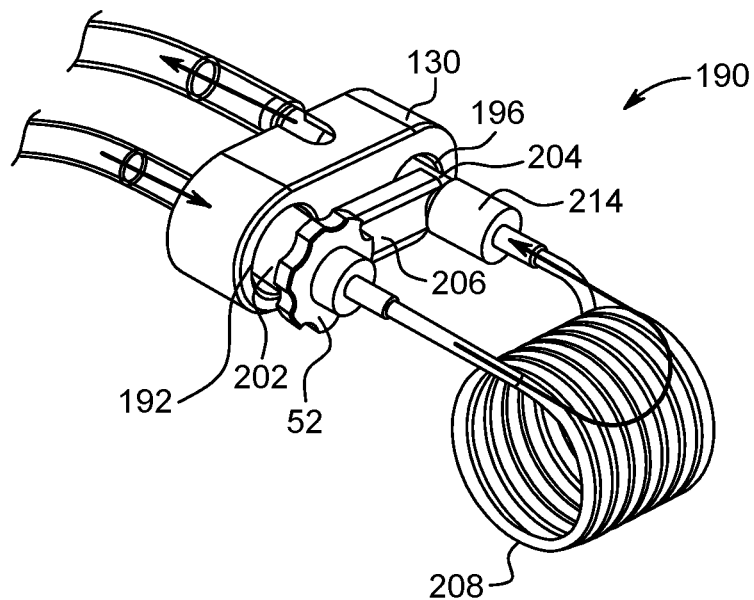
Figure 8D:
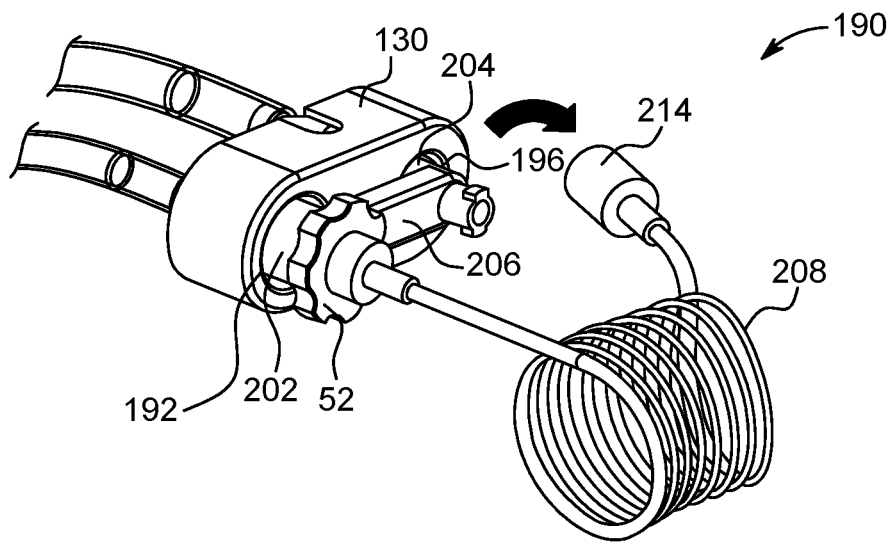
Figure 8E:
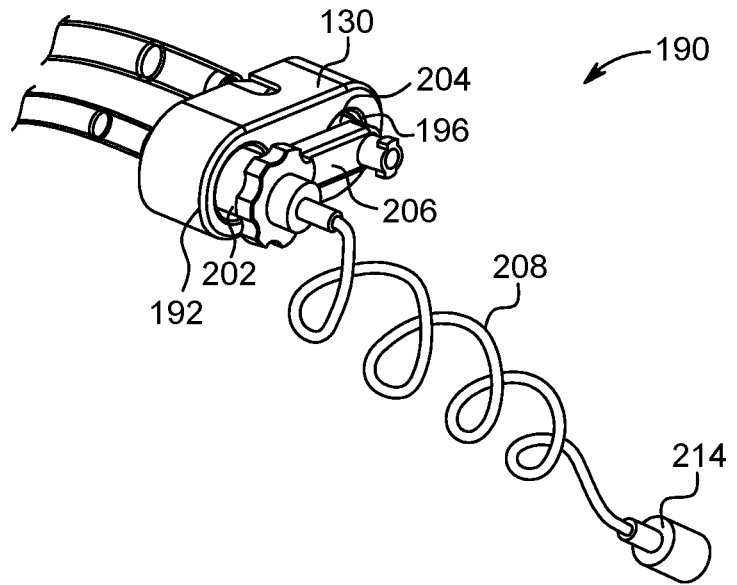
Figure 8F:
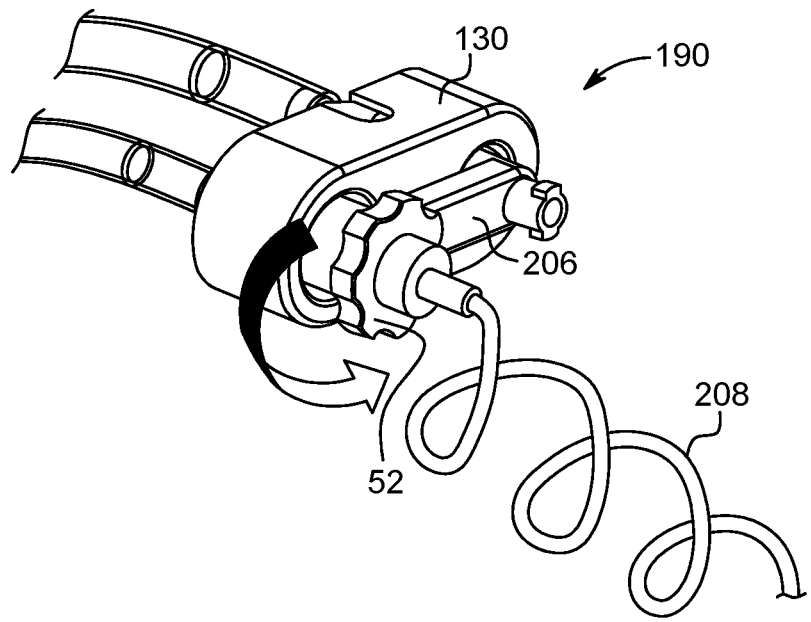

With reference to FIGS. 8A-8F, a method of operation of the embodiment of the connection assembly between the SUDS 190 and MUDS 130 depicted in FIGS. 6-7B will now be described in detail. In use, a medical technician or user removes the disposable SUDS 190 from its packaging and inserts the SUDS 190 into the corresponding MUDS 130. As described above, the SUDS 190 must be inserted in the correct orientation, such that the connection port 192 of the MUDS 130 engages the SUDS 190 fluid inlet port 202, and the waste inlet port 196 of the MUDS 130 engages the SUDS 190 waste outlet port 204. As shown in FIG. 8B, the medical technician then rotates the thumbwheel 52 to secure the SUDS 190 to the MUDS 130. Once the SUDS 190 is securely connected to the MUDS 130, the fluid injector system 100 (shown in FIG. 1) draws fluid into one or more of the plurality of syringes 132 of the MUDS 130 and performs an automatic priming operation (FIG. 8C) for removing air from the MUDS 130 and the SUDS 190. During such priming operation, fluid from the MUDS 130 is injected through the connection port 192 and into the tubing 208 of the SUDS 190. The fluid flows through the tubing 208 and through the waste outlet port 204 and into the waste reservoir 156. Once the automatic priming operation is completed, the medical technician disconnects the connector 214 from the waste outlet port 204 (FIG. 8D). The connector 214 may then be connected to the patient through a catheter, vascular access device, or additional fluid path set to facilitate fluid delivery to the patient (FIG. 8E). Once the fluid delivery is completed, the user disconnects the connector 214 rotates the thumbwheel 52 to remove the SUDS 190 from the MUDS 130 (FIG. 8F). The medical technician may then dispose of the SUDS 190. In certain embodiments, removing the SUDS 190 from the MUDS 130 causes reuse prevention features (not shown), such as tabs extending from a portion of the SUDS 190, to fold or break, preventing reinsertion of the SUDS 190.

Figure 9:
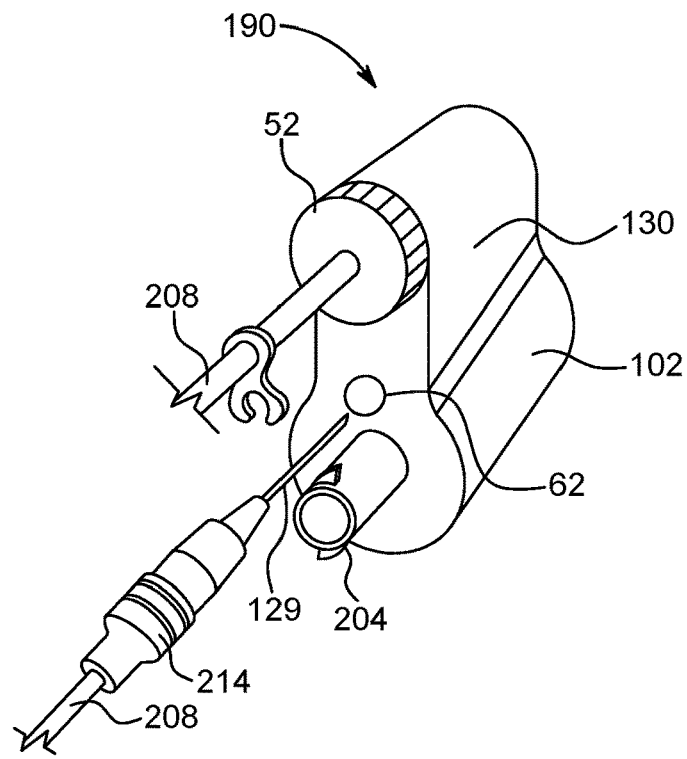
FIG. 9 is a perspective view of a single-use disposable set connector in accordance with another embodiment.

With reference to FIG. 9, a further embodiment of a connector assembly having a SUDS 190 and a MUDS 130 is illustrated. In this embodiment of the assembly, the SUDS 190 includes a cannula port 62 for receiving a needle cannula 129 connected to a connector 214. The cannula 129, used for fluid delivery to a patient, can be inserted into the cannula port 62 after being removed from the patient. The cannula port 62 may cover a contaminated end of the cannula 129 during disposal of the cannula 129. In this embodiment, the single-use enclosure 42 is desirably long enough so that the entire length of the needle cannula 129 may be inserted in the enclosure 42 for a safe disposal.

Figure 10A:
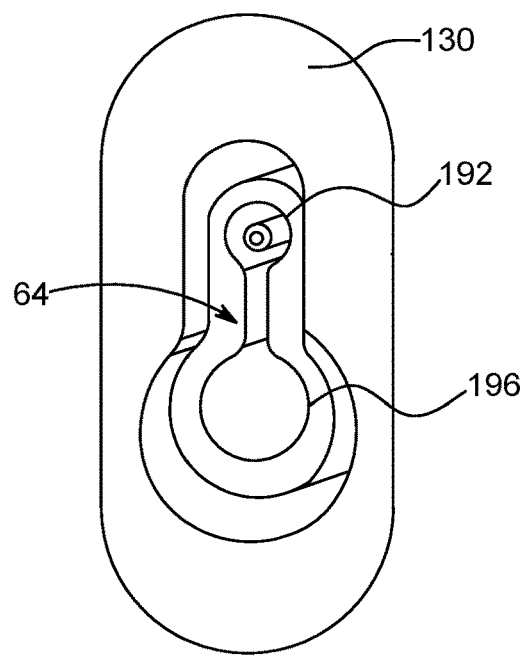
FIG. 10A is a perspective view of a port of a MUDS connector in accordance with one embodiment.
Figure 10B:
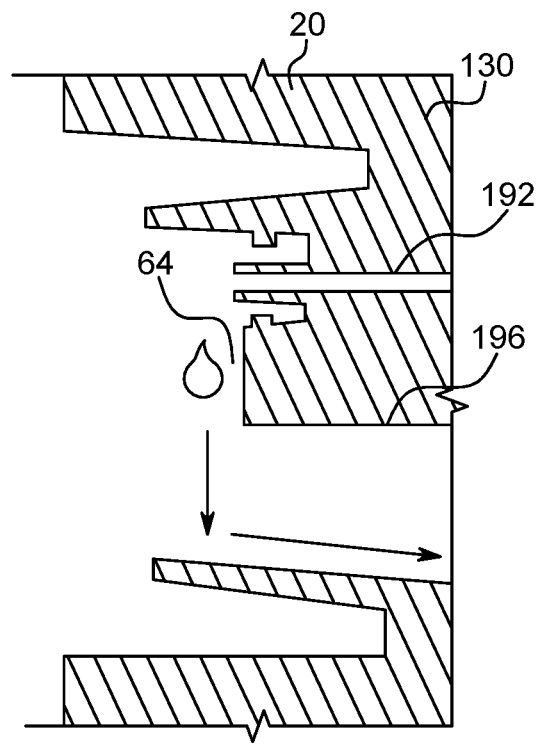
FIG. 10B is a schematic drawing of a cross-sectional view of the MUDS connector of FIG. 10A.
Figure 10C:
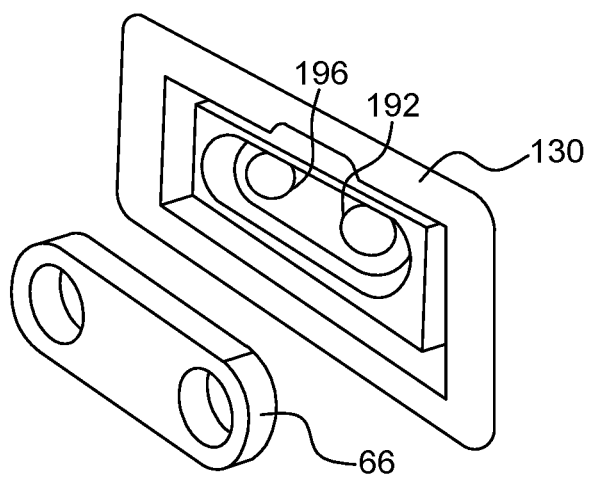
FIG. 10C is a schematic drawing of a MUDS connector having an absorbent pad attached thereto, according to another embodiment.

With reference to FIGS. 10A and 10B, a further embodiment of a connector assembly having a SUDS 190 and a MUDS 130 is illustrated. The connector assembly is provided in a vertical orientation with the connection port 192 of the MUDS 130 positioned above the waste inlet port 196. The MUDS 130 includes a drip channel 64 extending between the connection port 192 and waste inlet port 196. Any fluid leaking from the connection port 192 is directed downward through the drip channel 64 by gravity. The drip channel 64 exits into the waste inlet port 196. Accordingly, any fluid expelled from the drip channel 64 is directed through the waste inlet port 196 and is collected in the waste reservoir 156. Alternatively, the MUDS 130 may be provided with an absorbent material, such as an absorbent pad 66 shown in FIG. 10C, surrounding a portion of the connection port 192 and the waste inlet port 196. The absorbent material is provided to absorb any fluid drips during removal of the SUDS 190 for improved drip management.

Figure 11A:
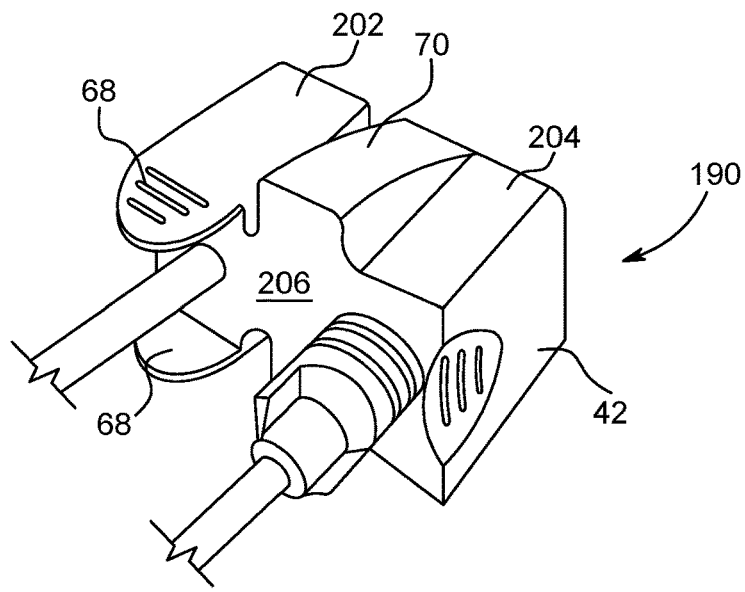
FIG. 11A is a perspective view of a single-use disposable set connector in accordance with another embodiment.
Figure 11B:
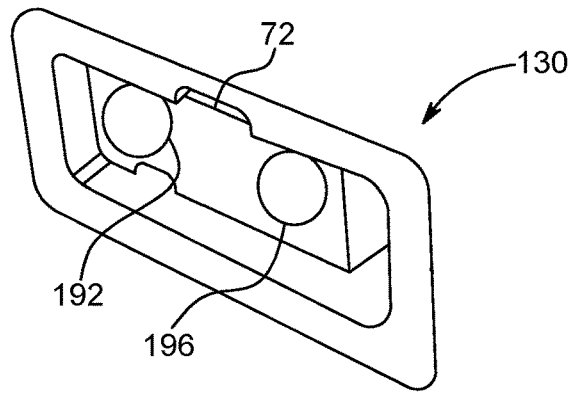
FIG. 11B is a perspective view of a MUDS connector in accordance with another embodiment.
Figure 11C:
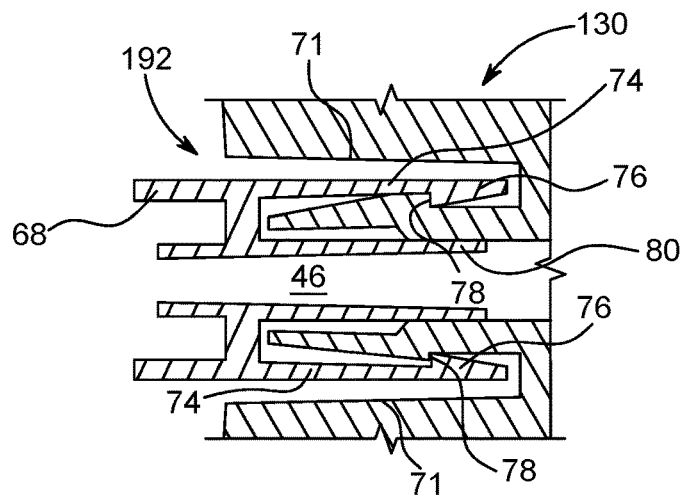
FIG. 11C is a cross-sectional view of a medical connector assembly, with the single-use disposable set connector of FIG. 11A inserted to the MUDS connector of FIG. 11B.

With reference to FIGS. 11A-11C, a further embodiment of the connector assembly having a SUDS 190 and a MUDS 130 having a plurality of press-fit connectors is illustrated. As shown in FIG. 11A, the SUDS 190 includes a fluid inlet port 202 and waste outlet port 204. The SUDS 190 includes disconnection tabs 68, rather than a thumbwheel. The SUDS 190 also includes an alignment structure 70 extending from the enclosure 42 of the SUDS 190 and is configured for insertion in a corresponding slot 72 of the MUDS 130 (shown in FIG. 11B).

Figure 12:
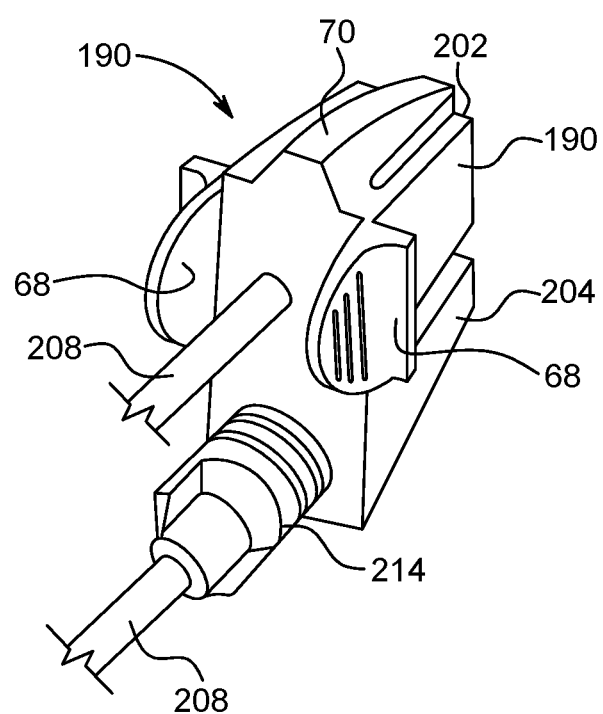
FIG. 12 is a front perspective view of a single-use disposable set connector in accordance with another embodiment.

As shown in the cross-sectional view depicted in FIG. 11C, the SUDS 190 is inserted into and aligned with the MUDS 130 by alignment channels 71. The disconnection tabs 68 are integrally formed with a tubular shroud 74 having an inwardly extending flange 76 at one end thereof. The shroud 74 surrounds a tubular conduit 80 on the SUDS 190. When the SUDS 190 is inserted into the MUDS 130, the flange 76 forms an interference engagement with a corresponding ridge 78 extending from a portion of the connection port 192 of the MUDS 130. The interference engagement creates a substantially fluid-tight connection between the MUDS 130 and the SUDS 190. Pressing the disconnection tabs 68 of the SUDS 190 disengages the flange 76 from the ridge 78 to allow a user to remove the SUDS 190 from the MUDS 130. With reference to FIG. 12, the connection assembly, having a MUDS 130 and SUDS 190 with disconnection tabs 68 described above, may also be provided in a vertical configuration.

Figure 13A:
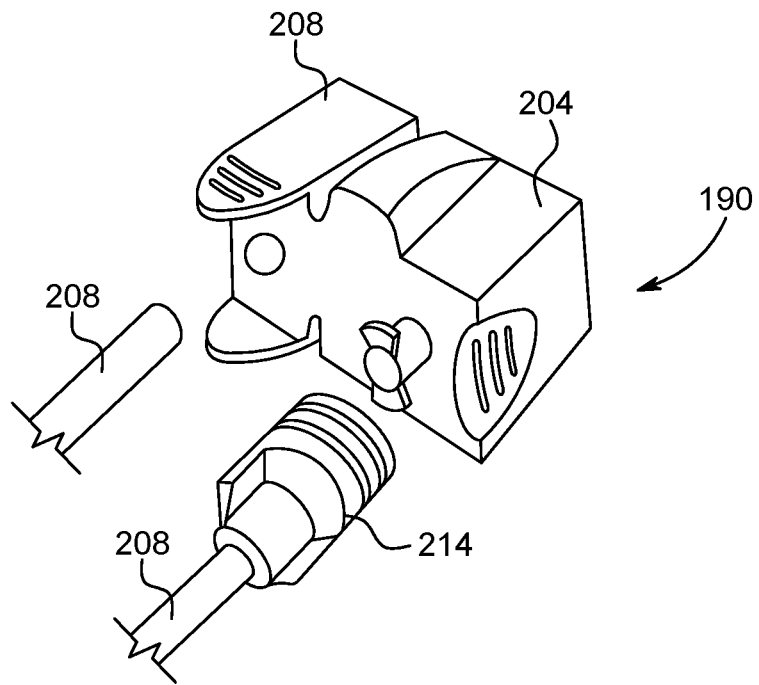
FIG. 13A is a perspective view of a single-use disposable set connector in accordance with another embodiment.
Figure 13B:
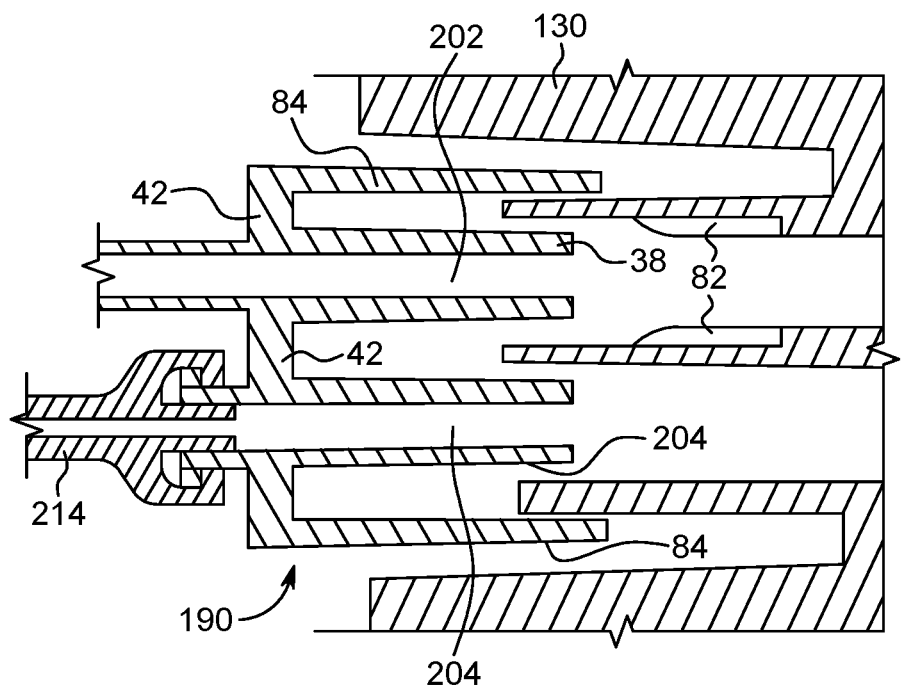
FIG. 13B is a cross-sectional view of a medical connection assembly including the single-use disposable set connector of FIG. 13A.
Figure 14A:
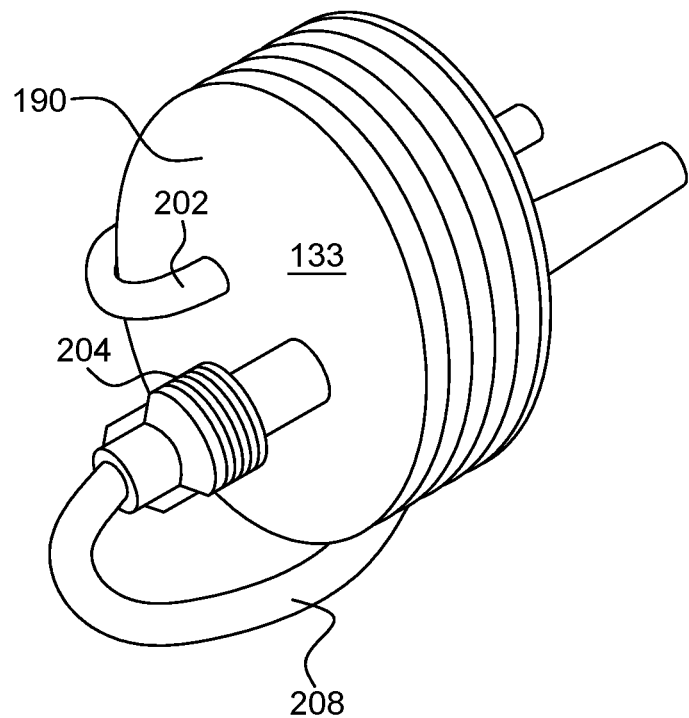
FIG. 14A is a perspective view of a single-use disposable set connector in accordance with another embodiment.
Figure 14B:
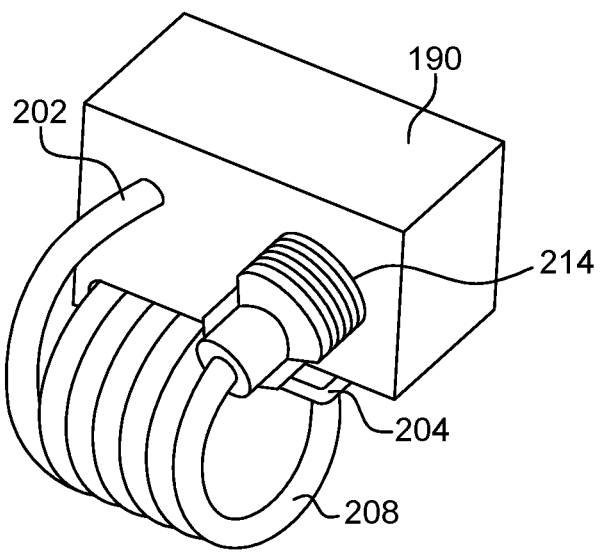
FIG. 14B is a perspective view of a single-use disposable set connector in accordance with another embodiment.
Figure 15A:
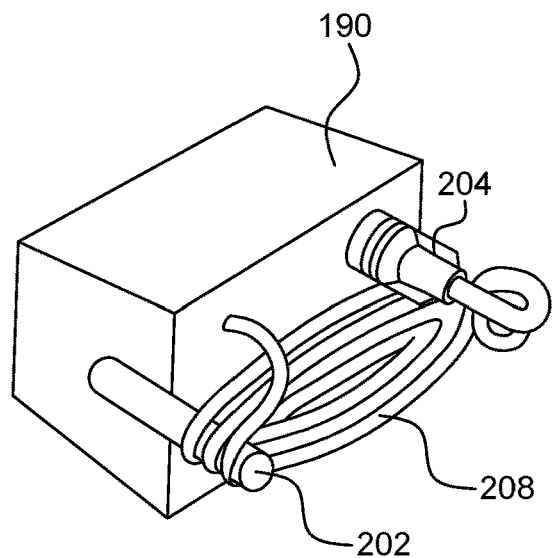
FIG. 15A is a perspective view of a single-use disposable set connector in accordance with another embodiment.
Figure 15B:
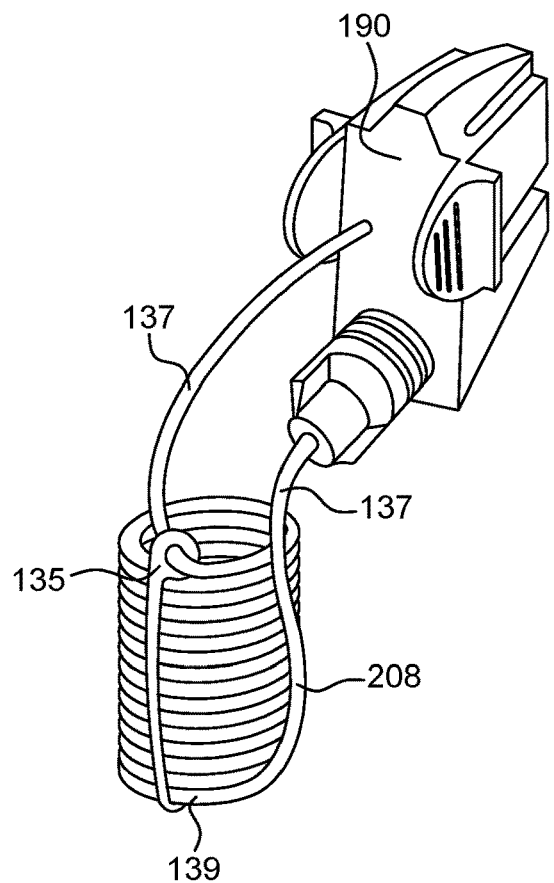
FIG. 15B is a perspective view of a single-use disposable set connector in accordance with another embodiment.

With reference to FIGS. 13A and 13B, a further embodiment of the connector assembly having a SUDS 190 and a MUDS 130 is illustrated. The MUDS 130 includes the connection port 192 and waste inlet port 196, as described in previous embodiments. The connection port 192 includes a co-molded sealing surface 82 for sealing between the SUDS 190 and the MUDS 130. The SUDS 190 includes external alignment surfaces 84, integrally formed with the enclosure 42, for correctly aligning the SUDS 190 and the MUDS 130. The alignment surfaces 84 also recess the fluid inlet port 202 and the waste outlet port 204 of the SUDS 190 to reduce the possibility of contamination prior to use.

Figure 16A:
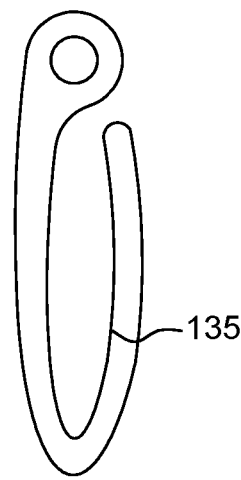
FIG. 16A is a side view of an external clip of the single-use disposable set connector of FIG. 15A.
Figure 16B:
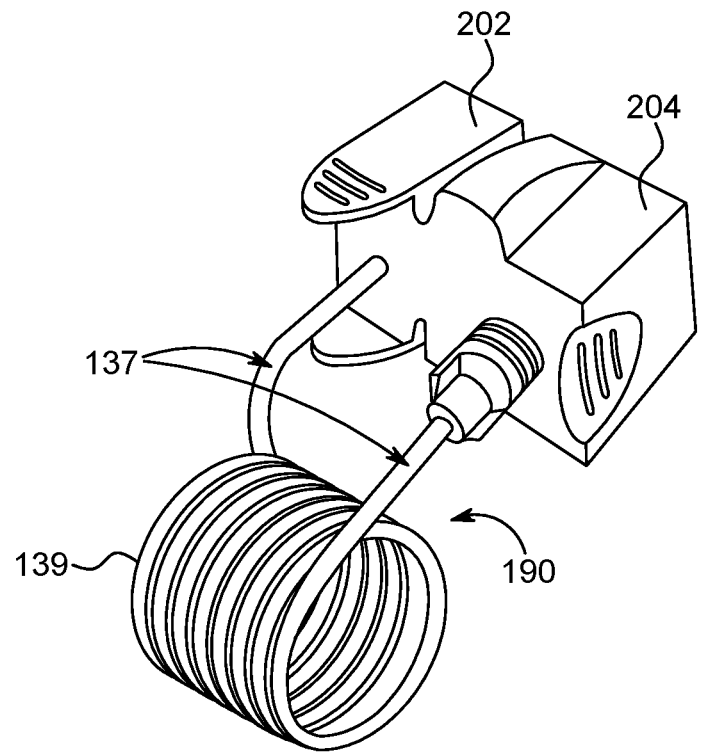
FIG. 16B is a perspective view of a single-use connector of a medical connector assembly, according to another embodiment.

With reference to FIGS. 14A-16B, various embodiments of the tubing 208 are illustrated. For example, the tubing 208 may be wound about a holding structure 133, such as a spool or frame member, for ensuring that the tubing 208 does not unwind while being removed from its packaging or when the SUDS 190 is being connected to the MUDS 130. With reference to FIG. 16A, the tubing 208 may further include a removable external clip 135. The clip 135 connects about the wound tubing 208 to prevent the tubing 208 from unwinding during removal from packaging or auto-priming. With reference to FIG. 16B, in a further embodiment, the tubing 208 is provided with uncoiled portions 137 to keep the tubing 208 away from the SUDS 190. A coiled portion 139 of the tubing 208 hangs below the un-coiled portions 137, when the SUDS 190 is connected to the MUDS 130.

Figure 17:
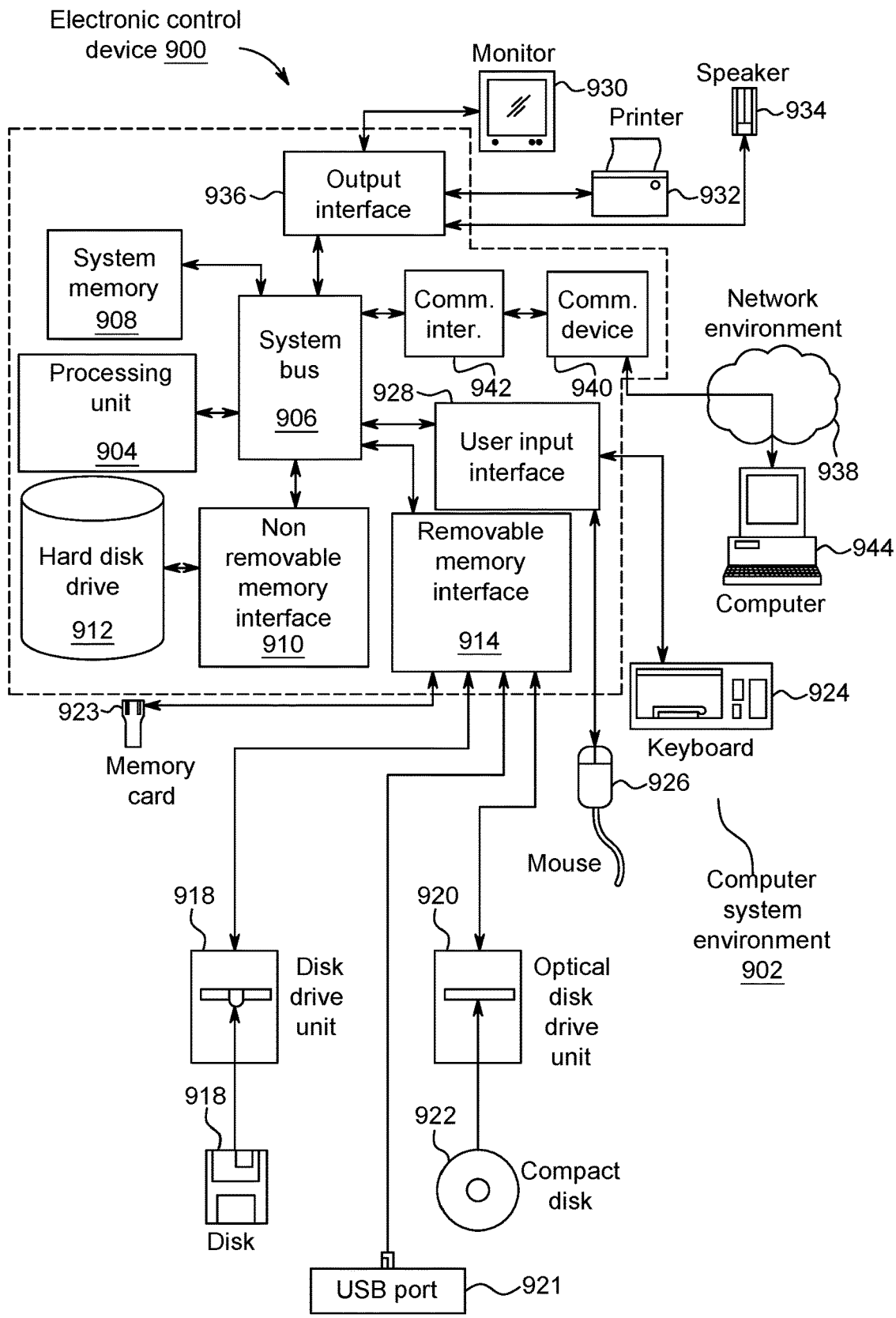
FIG. 17 is a schematic view of an electronic control system of a multi-fluid fluid injection system in accordance with another embodiment.

With reference to FIG. 17, an electronic control device 900 (shown in FIG. 17) may be associated with fluid injector system 100 to control the filling and delivery operations. In some embodiments, the electronic control device 900 may control the operation of various valves, piston members, and other elements to effect a desired filling or delivery procedure. For example, the electronic control device 900 may include a variety of discrete computer-readable media components. For example, this computer-readable media may include any media that can be accessed by the electronic control device 900, such as volatile media, non-volatile media, removable media, non-removable media, transitory media, non-transitory media, etc. As a further example, this computer-readable media may include computer storage media, such as media implemented in any method or technology for storage of information, such as computer-readable instructions, data structures, program modules, or other data; random access memory (RAM), read only memory (ROM), electrically erasable programmable read only memory (EEPROM), flash memory, or other memory technology; CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic control device 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic control device 900 further includes a system memory 908 with computer storage media in the form of volatile and non-volatile memory, such as ROM and RAM. A basic input/output system (BIOS) with appropriate computer-based routines assists in transferring information between components within the electronic control device 900 and is normally stored in ROM. The RAM portion of the system memory 908 typically contains data and program modules that are immediately accessible to or presently being operated on by the processing unit 904, e.g., an operating system, application programming interfaces, application programs, program modules, program data, and other instruction-based computer-readable codes.

With continued reference to FIG. 17, the electronic control device 900 may also include other removable or non-removable, volatile or non-volatile, transitory or non-transitory computer storage media products. For example, the electronic control device 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in the exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the electronic control device 900 via the system bus 906. The drives and their associated computer storage media, discussed above and illustrated in FIG. 17, provide storage of operating systems, computer-readable instructions, application programs, data structures, program modules, program data, and other instruction-based, computer-readable code for the electronic control device 900 (whether duplicative or not of this information and data in the system memory 908).

A user may enter commands, information, and data into the electronic control device 900 through certain attachable or operable input devices, such as the user interface 124 shown in FIG. 1, via a user input interface 928. Of course, a variety of such input devices may be utilized, e.g., a microphone, a trackball, a joystick, a touchpad, a touchscreen, a scanner, etc., including any arrangement that facilitates the input of data, and information to the electronic control device 900 from an outside source. As discussed, these and other input devices are often connected to the processing unit 904 through the user input interface 928 coupled to the system bus 906 but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic control device 900 through an output interface 936 coupled to the system bus 906. It is envisioned that any such peripheral output devices be used to provide information and data to the user.

The electronic control device 900 may operate in a network environment 938 through the use of a communications device 940, which is integral to the electronic control device 900 or remote therefrom. This communications device 940 is operable by and in communication with the other components of the electronic control device 900 through a communications interface 942. Using such an arrangement, the electronic control device 900 may connect with or otherwise communicate with one or more remote computers, such as a remote computer 944, which may be a personal computer, a server, a router, a network personal computer, a peer device, or other common network nodes, and typically includes many or all of the components described above in connection with the electronic control device 900. Using appropriate communication devices 940, e.g., a modem, a network interface or adapter, etc., the computer 944 may operate within and communicate through a local area network (LAN) and a wide area network (WAN), but may also include other networks such as a virtual private network (VPN), an office network, an enterprise network, an intranet, the Internet, etc.

As used herein, the electronic control device 900 includes, or is operable to execute appropriate custom-designed or conventional software to perform and implement the processing steps of the method and system of the present disclosure, thereby forming a specialized and particular computing system. Accordingly, the presently-invented method and system may include one or more electronic control devices 900 or similar computing devices having a computer-readable storage medium capable of storing computer-readable program code or instructions that cause the processing unit 904 to execute, configure, or otherwise implement the methods, processes, and transformational data manipulations discussed hereinafter in connection with the present disclosure. Still further, the electronic control device 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

It will be apparent to one skilled in the relevant arts that the system may utilize databases physically located on one or more computers which may or may not be the same as their respective servers. For example, programming software on electronic control device 900 can control a database physically stored on a separate processor of the network or otherwise.

In some embodiments, the electronic control device 900 may be programmed so that automatic refill occurs based upon a preprogrammed trigger minimum volume in the respective syringes 132. For example, when the volume of fluid remaining in at least one of the syringes 132 is less than a programmed volume, a syringe refill procedure is automatically initiated by the electronic control device 900. The electronic control device 900 associated with the fluid injector system 100 may determine that the preprogrammed trigger minimum volume has been reached by tracking the fluid volume dispensed from the respective syringes 132 during operation of the fluid injector system 100. Alternatively, fluid level sensors may be incorporated into the fluid injector system 100 and inputs from these fluid level sensors may be provided to the electronic control device 900 so that the electronic control device 900 may determine when the preprogrammed trigger minimum volume has been reached in at least one of the syringes 132. The fill volume and rate of refill can be preprogrammed in the electronic control device 900. The automatic refill procedure can be stopped either automatically by the electronic control device 900 or may be manually interrupted. In addition, an automatic refill procedure may be initiated when, at the completion of a fluid injection procedure, there is not enough fluid in at least one of the syringes 132 to perform the next programmed fluid injection procedure.

During a refill procedure it is possible that one or more of the bulk fluid sources 120 associated with the respective syringes 132 may become empty, (e.g., initially lack sufficient fluid to complete a full refill of the one or more syringes 132). A replacement bulk fluid source 120 is, therefore, necessary and replacement of such bulk fluid source 120 is desirably made quickly. The fluid injector system 100 may have an indicator, such as an audible and/or visual indicator, to indicate to the operator that a change of the bulk fluid source 120 is necessary before the fluid injector system 100 may be used.

While several embodiments of single-use disposable set connectors are shown in the accompanying figures and described hereinabove in detail, other embodiments will be apparent to, and readily made by, those skilled in the art without departing from the scope and spirit of the disclosure. For example, it is to be understood that this disclosure contemplates that, to the extent possible, one or more features of any embodiment can be combined with one or more features of any other embodiment. Accordingly, the foregoing description is intended to be illustrative rather than restrictive.

What is claimed is:

1. A medical connector comprising:
   a fluid inlet port configured for removable engagement with a connection port of a multi-use disposable set (MUDS) to establish a fluid connection beteen the fluid inlet port and the connection port of the MUDS;
   a locking mechanism for reversibly locking the medical connector with the connection port, the locking mechanism having a flexible tab that is deflectable between an engaged position and a disengaged position by deflecting at least a portion of the flexible tab;
   at least one sensing element in the form of at least one sensing fin extending vertically from an upper surface of the flexible tab of the locking mechanism, wherein at least one side of the at least one sensing fin has one or more reflective surfaces for reflecting visible or infrared light, wherein the one or more reflective surfaces of the at least one sensing fin are configured to interact with at least one sensor on a fluid injector system when the locking mechanism is locked in the engaged position the medical connector is securely connected to the connection port of the MUDS, and the fluid inlet port is in fluid communication with the connection port;
   a patient fluid line connected, at a first end, to the fluid inlet port and having a fluid line connector at a second end configured for connection to a patient catheter to establish a fluid connection between the connection port and the patient catheter,
   a one-way valve configured for maintaining unidirectional flow through the fluid inlet port into the patient fluid line, wherein the at least one sensing element is configured to indicate that the medical connector has been inserted or installed in the connection port when the at least one sensing element is detected by the at least one sensor.

2. The medical connector of claim 1, wherein the one or more reflective surfaces are configured to reflect the visible or infrared light to be detected by the at least one sensor.

3. The medical connector of claim 1, wherein the at least one sensing element is a breakable sensor element configured to fold or break when the medical connector is removed from the MUDS.

4. The medical connector of claim 1, wherein the at least one sensing element is formed on the flexible tab.

5. The medical connector of claim 4, wherein the flexible tab forms a releasable locking engagement with a receiving slot on the connection port of the MUDS when in the engaged position.

6. The medical connector of claim 1, wherein the medical connector has an asymmetrical shape such that the medical connector is connectable with the connection port of the MUDS in one orientation only.

7. The medical connector of claim 6, further comprising at least one fin to prevent erroneous connection of the medical connector with the MUDS.

8. The medical connector of claim 1, further comprising a waste outlet port configured for removable engagement with a waste inlet port of the fluid injector system to establish fluid connection therewith, and
wherein the fluid line connector is further configured for removable engagement with the waste outlet port while maintaining sterility of the second end.

9. The medical connector of claim 8, wherein the fluid line connector is configured to be in fluid communication with the waste outlet port when engaged with the waste outlet port.

10. The medical connector of claim 1, wherein the fluid inlet port has at least one seal for forming a fluid-tight connection between the fluid inlet port and the connection port.

11. A single-use disposable set (SUDS) connector, the SUDS connector comprising:
a fluid inlet port configured for removable engagement with a connection port of a multi-use disposable set (MUDS) to establish a fluid connection between the fluid inlet port and the connection port of the MUDS;
a locking mechanism configured for removably securing the SUDS connector to the MUDS, the locking mechanism having a flexible tab that is deflectable between an engaged position and a disengaged position by deflecting at least a portion of the flexible tab;
at least one sensing fin extending vertically from an upper surface of the flexible tab, wherein at least one side of the at least one sensing fin has a reflective surface for reflecting visible or infrared light, wherein the reflective surface of the at least one sensing fin is configured to interact with at least one sensor on a fluid injector system when the flexible tab is in the engaged position and the SUDS connector is securely connected to the connection port of the MUDS; and
a patient fluid line connected, at a first end, to the fluid inlet port and having a fluid line connector at a second end configured for connection to a patient catheter to establish a fluid connection between the connection port and the patient catheter,
wherein the at least one sensing fin is configured to indicate that the SUDS connector has been properly inserted or installed in the connection port, wherein the at least one sensing fin is configured such that detection of the at least one sensing fin by the at least one sensor initiates an automatic priming sequence to prime the patient fluid line with a fluid,
wherein the patient fluid line is configured for unidirectional fluid flow from the first end to the second end.

12. A method of priming a single-use disposable set (SUDS) connector, the method comprising:
fluidly connecting a fluid inlet port of the SUDS connector with a connection port of a multi-use disposable set (MUDS);
establishing fluid communication through a patient fluid line between the fluid inlet port of the SUDS connector at a first end of the patient fluid line and a fluid line connector at a second end of the patient fluid line;
detecting, by at least one sensor on a fluid injector system, the presence or absence of at least one sensing element in the form of a sensing fin extending vertically from an upper surface of a flexible tab of a locking mechanism of the SUDS connector, wherein detecting the presence of the sensing fin comprises detecting reflection of visible or infrared light due to one or more reflective surfaces on the sensing fin to indicate that the SUDS connector has been properly inserted or installed in the connection port; and
if the presence of the sensing fin is detected by the at least one sensor, automatically priming the SUDS connector by delivering fluid from the fluid inlet port to the fluid line connector through the patient fluid line.

13. The method of claim 12, further comprising:
connecting the fluid line connector at the second end of the patient fluid line of the primed SUDS connector to a patient catheter to establish fluid communication from the fluid inlet port of the SUDS connector to the patient catheter.

14. The method of claim 12, wherein the fluid line connector is removably connected to a waste inlet port, and wherein the waste inlet port is in fluid communication with a waste outlet port of the fluid injector system.

15. The method of claim 12, wherein detecting the presence or absence of the sensing fin on the SUDS connector comprises detecting the presence or absence of the one or more reflective surfaces on the sensing fin of the at least one sensing element by the at least one sensor.

16. The method of claim 12, wherein, if the absence of the at sensing fin on the SUDS connector is detected, the method further comprises preventing automatic priming of the SUDS connector, halting an injection procedure, and indicating on the fluid injector system that no SUDS connector is detected.

17. A medical connector comprising:
a fluid inlet port configured for removable engagement with a connection port of a multi-use disposable set (MUDS) to establish a fluid connection between the fluid inlet port and the connection port of MUDS;
at least one sensing element configured to interact with at least one sensor on a fluid injector system, wherein the at least one sensing element comprises at least one sensing fin extending vertically from an upper surface of a flexible tab of a locking mechanism of the medical connector, wherein at least one side of the at least one sensing fin has a reflective surface for reflecting visible or infrared light; and
a patient fluid line connected, at a first end, to the fluid inlet port and having a fluid line connector at a second end configured for connection to a patient catheter to establish a fluid connection between the connection port and the patient catheter, wherein the at least one sensor is configured to indicate to a controller of the fluid injector system that the medical connector has been properly inserted or installed in the connection port when a presence of the at least one sensing fin is detected by the at least one sensor.

18. The medical connector of claim 17, wherein the medical connector has an asymmetrical shape such that the medical connector is connectable with the connection port of the MUDS in one orientation only.

* * * * *

UNITED STATES PATENT AND TRADEMARK OFFICE
CERTIFICATE OF CORRECTION

| | | |
|---|---|---|
| PATENT NO. | : 12,233,230 B2 | Page 1 of 1 |
| APPLICATION NO. | : 16/773150 | |
| DATED | : February 25, 2025 | |
| INVENTOR(S) | : Sokolov et al. | |

It is certified that error appears in the above-identified patent and that said Letters Patent is hereby corrected as shown below:

In the Specification

In Column 6, Line 36, delete "also" and insert -- also be --, therefor.

In the Claims

In Column 18, Line 40, in Claim 1, delete "beteen" and insert -- between --, therefor.
In Column 18, Line 56, in Claim 1, delete "position the" and insert -- position, the --, therefor.
In Column 20, Line 47, in Claim 16, delete "at sensing" and insert -- sensing --, therefor.
In Column 20, Line 56, in Claim 17, delete "of MUDS;" and insert -- of the MUDS; --, therefor.

Signed and Sealed this
Sixth Day of May, 2025

Coke Morgan Stewart
*Acting Director of the United States Patent and Trademark Office*